United States Patent [19]
Gerardi et al.

[11] Patent Number: 5,195,046
[45] Date of Patent: Mar. 16, 1993

[54] METHOD AND APPARATUS FOR STRUCTURAL INTEGRITY MONITORING

[76] Inventors: Joseph J. Gerardi; Gail A. Hickman, both of 81 Crystal Dr., Dryden, N.Y. 13053

[21] Appl. No.: 559,482

[22] Filed: Jul. 30, 1990

Related U.S. Application Data

[63] Continuation-in-part of Ser. No. 295,722, Jan. 10, 1989, Continuation-in-part of Ser. No. 518,043, May 4, 1990.

[51] Int. Cl.$^5$ .................. G06F 15/20; G01H 1/00
[52] U.S. Cl. ............................. 364/506; 73/583; 73/659; 364/550
[58] Field of Search ........... 73/579, 583, 602, 659, 73/768, 771, 775; 364/506, 507, 508, 550

[56] References Cited

U.S. PATENT DOCUMENTS

| | | | |
|---|---|---|---|
| RE. 31,750 | 11/1984 | Morrow | 364/508 |
| 2,440,198 | 4/1948 | Green | 73/147 |
| 2,541,512 | 2/1951 | Hahn | 73/170 R |
| 2,543,020 | 2/1951 | Hess | 73/189 |
| 2,789,281 | 4/1957 | Short et al. | 340/582 |
| 2,800,647 | 7/1957 | Baerwald et al. | 340/582 |
| 3,240,054 | 3/1966 | Roth | 73/576 |
| 3,362,663 | 1/1968 | Wehrmann | 244/130 |
| 3,383,914 | 5/1968 | MacArthur | 73/147 |
| 3,453,873 | 7/1969 | Lambert | 73/775 X |
| 3,915,015 | 10/1975 | Crane et al. | 73/865.4 |
| 4,128,011 | 12/1978 | Savage | 73/579 |
| 4,342,229 | 8/1982 | Massa | 73/579 |
| 4,372,157 | 2/1983 | Caruthers et al. | 73/147 |
| 4,383,446 | 5/1983 | Roeder et al. | 73/579 |
| 4,429,580 | 2/1984 | Testa et al. | 73/775 X |
| 4,435,695 | 3/1984 | Maris | 73/147 X |
| 4,461,178 | 7/1984 | Chamuel | 73/599 |
| 4,507,705 | 3/1985 | Hoshino et al. | 73/579 X |
| 4,516,747 | 5/1985 | Lurz | 244/204 |
| 4,545,553 | 10/1985 | Finke et al. | 244/134 D |
| 4,553,137 | 11/1985 | Marxer et al. | 340/582 |
| 4,568,922 | 2/1986 | Schwippert et al. | 340/582 |
| 4,570,881 | 2/1986 | Lustenberger | 244/134 F |
| 4,592,229 | 6/1986 | Butefisch et al. | 73/147 |
| 4,604,612 | 8/1986 | Watkins et al. | 340/582 |
| 4,611,492 | 9/1986 | Koosmann | 73/579 |
| 4,631,958 | 12/1986 | Van Cauwenberghe et al. | 73/189 |
| 4,631,959 | 12/1986 | Motycka | 73/189 |
| 4,688,421 | 8/1987 | Pzsolla | 73/147 |

(List continued on next page.)

FOREIGN PATENT DOCUMENTS

| | | | |
|---|---|---|---|
| 883836 | 11/1981 | U.S.S.R. | 73/170 R |
| 1012143A | 4/1983 | U.S.S.R. | 73/189 |

OTHER PUBLICATIONS

Richard G. O'Lone, "Special Report: The World Airline Fleet Grows Older", *Aviation Week and Space Technology*, vol. 131, No. 4, (Jul. 24, 1989) pp. 42, 43, 45.

M. A. Donelan and J. Motycka "Miniature Drag Sphere Velocity Probe", *Rev. Sci Instrum.*, 49(3) Mar., 1978, pp. 298-304.

J. G. Dessureault and D. F. Knox "Design of a Tri-Axial Anemometer for Measurement of Atmospheric Turbulence Over Water", *Ocean Engineering*, vol. 7, No. 4 (1980) pp. 521–537.

(List continued on next page.)

*Primary Examiner*—Edward R. Cosimano
*Attorney, Agent, or Firm*—Pennie & Edmonds

[57] ABSTRACT

A system is disclosed for monitoring a structure and detecting disturbances and faults associated with such structure. The system includes an actuation device for mechanically exciting the structure, a sensing device for transducing vibrations experienced by the structure, and digital signal processing means for processing signals output by the sensing device. The response of the structure due to the mechanical excitation is analyzed and a baseline or normal response is determined. Vibrations of the structure are then analyzed and compared to the normal response of the structure and the nature of disturbances identified. Another aspect of the invention relates to a system for monitoring cracks, strains and the like and includes a continuity/strain sensor having a piezoelectric layer, and first and second low resistance layers. By suitably monitoring sensors in accordance with the invention, the magnitude as well as the location of a force can be determined.

36 Claims, 18 Drawing Sheets

U.S. PATENT DOCUMENTS

| | | | |
|---|---|---|---|
| 4,690,353 | 9/1987 | Haslim et al. | 244/134 D |
| 4,730,485 | 3/1988 | Franklin et al. | 73/189 |
| 4,732,351 | 3/1988 | Bird | 244/134 D |
| 4,766,369 | 8/1988 | Weinstein | 244/134 F |
| 4,775,118 | 10/1988 | Daniels | 244/134 D |
| 4,786,020 | 11/1988 | Franke et al. | 244/204 |
| 4,788,869 | 12/1988 | Li | 73/189 X |
| 4,802,642 | 2/1989 | Mangiarotty | 244/204 X |
| 4,805,457 | 2/1989 | Oates et al. | 73/579 |
| 4,891,628 | 1/1990 | Zuckerman | 340/582 |
| 5,068,800 | 11/1991 | Brook et al. | 364/506 |

OTHER PUBLICATIONS

Jean-Guy Dessureault and David R. Harvey "The Design of a Thrust Anemometer For Drifting Buoy", *Conference: Oceans '81, Conference Record, (IEEE)* Boston, Mass., Sep. 16-18, 1981 pp. 411-414.

Kovattana "Triaxial Force Sensor", *Proceedings of the 1982 Carnahan Conference on Security Technology*, May 1982, pp. 71-79.

Olsson et al., "Assessment of the Piezo-Electric Foil as a Mean of Monitoring the Wall Turbulence", *The Aeronautical Research Institute of Sweden (FFA)*, Stockholm, Document No. FFATN 1985-60, 1985, pp. 1-30.

A. Bertelrud, "Use of Hot film Sensors and Piezoelectric Foil for Measurement of Local Skin Friction", *The 12th International Congress on Instrumentation in Aerospace Simulation Facilities (ICIASF)*, Williamsburg, Vir., Jun. 22-25, 1987, pp. 1-5 (FIGS. 1-22).

W. B. Scott, "New Stall Detection System Measures Intensity of Turbulent Airflow Over Wing", *Aviation Week & Space Technology*, Jan. 11, 1988, pp. 57-59.

W. B. Scott "Air Force Funding Joint Studies to Develop 'Smart Skin' Avionics", *Aviation Week & Space Technology*, Apr. 18, 1988, pp. 65.

Wusk et al. "An Arrayed Hot-Film Sensor for Detection of Laminar Boundary-Layer Flow Disturbance Spatial Characteristics", *AIAA/NASA/AFWAL Sensors & Measurement* Technologies Conference, Atlanta, Ga., Sep. 1-9, 1988, pp. 1-11.

J. S. Heyman and R. S. Rogowski "Fiber Optic Sensor Technology—An Opportunity for Smart Aerospace Structures," *AIAA/NASA/AFWAL Conference on Sensors and Measurements Techniques for Aeronautical Applications*, Atlanta, Ga., Sep. 7-9, 1988, pp. 1-5.

Regowski et al. "The Evolution of 'Smart' Composite Material", *NASA Tech. Briefs*, Oct., 1988, pp. 20-22.

Goldberg and Lardiere, Jr., "Developments in Expulsive Separation Ice Protection Blankets", *AIAA, 27th Aerospace Sciences Meeting*, Reno, Nev., Jan. 9-12, 1989, pp. 1-5.

(LONGITUDINAL MODE)

(THICKNESS MODE)

RIVET LINE GROUND TESTS

RIVET LINE TESTS

METHOD AND APPARATUS FOR STRUCTURAL INTEGRITY MONITORING

STATEMENT REGARDING GOVERNMENT FUNDED RESEARCH

This invention was made with Government support under NAS1-19014 and NAS3-25200 awarded by the National Aeronautics and Space Administration. The Government has certain rights in this invention.

CROSS-REFERENCE TO RELATED APPLICATIONS

This is a continuation-in-part of U.S. patent application Ser. No. 07/295,722 filed on Jan. 10, 1989, entitled "Smart Skin Ice Detection and De-Icing System", incorporated herein by reference, and a continuation-in-part of U.S. patent application Ser. No. 07/518,043 filed on May 4, 1990, entitled, "Improved Piezoelectric Sensor", also incorporated herein by reference.

BACKGROUND OF THE INVENTION

1. Technical Field

This invention relates generally to methods and devices for monitoring of structures and more particularly to use of dispersed sensing and signal processing modules adapted for attachment to structures such as airplane or spacecraft structural members. Such devices are particularly well suited for the detection and/or monitoring of fatigue cracks, corrosion, ice accretion, and structural damage associated with aircraft. The devices may also be employed to monitor strains in structures such as buildings, ships, underwater vessels, storage tanks, dams and bridges. Additionally, the devices may be used in an active mode in which the devices are excited electronically to generate forces that can be used in the control of structures, as well as to actuate, remove, or modify matter on the surface of the structure. These devices may also be applied to structures for use as intelligent switches or surface scanning devices.

2. Description of the Prior Art

A significant amount of effort and expense has been expended in the last few years in the field of aircraft testing and maintenance so as to provide the population with a safer means of travel. In light of disastrous aircraft crashes and the fatalities associated therewith which occur unnecessarily and all too often, and the concomitant ensuing liability suits, the future will surely include more stringent testing and maintenance procedures. See "Special Report: The World Airline Fleet Grows Older", *Aviation Week and Space Technology*, Vol. 131, No. 4 (Jul. 24, 1989) pp. 42–95.

Many aircraft crashes resulting from structural failure can be prevented by use of a health monitoring system which detects and monitors fatigue cracks, corrosion, ice accretion, as well as structural integrity. While recently developed technology has made some advances, even the most current systems require extensive modification of aircraft structure, cannot monitor large areas, are prone to misinterpretation, suffer from inaccuracy, are too complex, bulky and not self-contained, or require external power sources. Additionally, known systems are generally very limited in what they measure. For example, systems are known which detect ice formation on aircraft wings, however, they do not detect or monitor fatigue, cracks, corrosion, or structural integrity.

An on-line autonomous health monitoring system capable of monitoring a plurality of parameters is clearly desirable. Specific illustrative areas which will especially benefit from such a health monitoring system will now be discussed in detail sufficient to enable one to understand the context within which the present invention preferably operates and the problems which must be overcome.

Cracks, Corrosion and Metal Fatigue

Shortcomings in the methods presently used to detect cracks, corrosion and metal fatigue in aircraft are complicating airline efforts to ensure the safety of aging aircraft. Current techniques are so costly and time consuming that retiring some of the oldest jets in commercial airlines' aging fleets may be more effective than maintaining them. Airlines presently depend largely on visual inspections. However, many cracks are difficult to spot with the naked eye until they become large enough to constitute a potential hazard. Even sophisticated techniques sometimes miss surface fatigue cracks. In a recent crash of an air Canada DC-9, expert X-ray examination passed over some telltale cracks, and a hole was blown in the aircraft's aft bulkhead during flight.

Ice Accretion

Ice accretion, or buildup, on aircraft structural members such as airfoils can have deleterious effects on flight performance. Lift decreases, thrust falls off, drag and weight increase, and stall speed dramatically increases. Undetected ice on airfoils has caused a number of catastrophic crashes in recent years. This hazard continues to threaten general aviation and high performance commercial jet aircraft. In the past, there has been no adequate direct means available to an aircraft pilot to detect icing on airfoil lifting surfaces. Known ice formation sensors are inadequate for use with modern aircraft. Known sensors suffer from being limited to detection of only localized ice accretion, from being too cumbersome, requiring energy sources, not retrofittable to existing airfoils, etc.

Space debris, micro-meteors

Material degradation and contamination due to long-term exposure to the space environment is a serious concern for spacecraft. Hazards include atomic oxygen, radiation, charged particles, thermal cycling, micro-meteors and debris, vacuum, and contamination. Physical effects include surface erosion, outgassing, and structural modification. Future space structures, whether capable of self-powered flight or not, will require some type of sensing system to detect damage which occurs to the structure and provide feedback information to control mechanisms. An advanced Health Monitoring System (HMS) that continuously monitors the dynamic properties of certain structures of a spacecraft or the like will be required.

Accordingly, the present invention provides an integrated, low weight, health assessment system for aircraft and other structures. Advantageously, the present invention will significantly increase the safety and reliability of long duration space missions. This invention may be used in conjunction with a control system to provide a damping force to reduce structural vibrations inherent in large structures. Advantageously, the present invention enables aircraft and spacecraft to be replaced when it is no longer economically feasible to repair them, and not based on statistics or the mere passage of time. Additionally, the present invention enables determination of the location and magnitude of force applied to a structure employing a single sensor and actuator.

SUMMARY OF THE INVENTION

An illustrative device, or sensor module, in accordance with the invention includes a plurality of piezoelectric transducers. These transducers convert mechanical motion experienced by aircraft structures into corresponding electrical signals. These transducers also convert dynamic strains such as that produced by cracks or corrosion into electrical signals. These electrical signals provide useful information in the detection of structural flaws, corrosion and ice accretion. By detecting and recording the nature of mechanical vibrations, patterns or signatures can be determined which provide detailed fingerprint of the structure. A physical change in the structure will alter its signature. Recording the signature and building a database of key parameters having characteristics relating to strain, acceleration, vibration, etc. enables an electronic blueprint to be formed. Such electronic blueprint of an individual aircraft or part thereof constitutes a signature against which to measure later performance. For example, a change in an aircraft's vibration profile could warn of upcoming problems.

A principle underlying the operation of the Health Monitoring System (HMS) of the present invention is the use of specimen vibration signatures to determine mechanical and thermal properties. A specimen vibration signature is derived from the dynamic response or reaction of a structure to a stimulus. Such dynamic response typically is the varying electrical output of transducers attached to the structure. Vibration signatures may arise from a known and controlled stimulus and/or from stimuli generally beyond one's control such as engine noise experienced by aircraft during flight. Damage to a structure often manifests itself as a change in the dynamic response of the structure, corresponding to changes in the physical properties of the structure and changes in the vibration signature. The HMS applies this concept to obtain dynamic response characteristics corresponding to failure or damage of structural components. Specifically, the HMS mechanically excites the structure and monitors the dynamic response of the structure through sensors or feedback transducers to determine the structure's response, including a baseline or normal response. The excitation energy is preferably in the form of a single pulse which generates a wideband frequency range of vibration of the structure. The feedback transducers are preferably piezoelectric film transducers.

Pattern recognition techniques are used to process vibration signals and classify the type and location of structural damage which gives rise to vibration signals different from baseline vibration signals. These techniques analyze vibration signals corresponding to the dynamic response of the structure in a pattern space of data corresponding to features which characterize the vibration signals. Such vibration signals may be, for example, digitized data obtained from the dynamic response of the structure.

In addition to the pattern recognition techniques, key components of the overall health monitoring system include intelligent sensor modules, a host central processing unit (CPU), and a high speed databus. The sensor module contains an actuation mechanism to generate a physical impulse and apply it to the structure, and feedback transducer(s) and signal processing circuitry to detect the corresponding vibration signals, process them, and transmit the preferably digitized data to the host CPU when queried. The sensor module is also provided with an embedded processor for controlling the actuation mechanism as well as for data acquisition. The host CPU executes pattern recognition software which distinguishes among fatigue cracks, rivit line failure, ice or material buildup on the structure, and other disturbances.

Advantageously, sensor modules constructed in accordance with the present invention exhibit distributed capability for wide area detection of structural faults and the like. Sensor modules are located throughout the aircraft or spacecraft structure and are connected to the host CPU by the high speed databus which preferably is a high speed bidirectional serial databus. The databus also includes power lines for the sensor modules for actuation and signal processing. This design enables a low voltage lightweight system to be implemented on aircraft and spacecraft with a relatively simple bus structure. By including signal processing and power converting circuitry in the sensor module, complex cables, high voltage problems and wiring problems are eliminated. Performing data acquisition and limited signal processing at the sensor module also saves valuable CPU time and permits superior system performance on large airframes.

The sensor module's actuation mechanism creates an impulse force by rapidly discharging a capacitor into a pair of opposing electromagnetic (EM) coils. The coils are separated by a gap that widens when the current induced EM force field is applied, transmitting an impulse force to the structural member to which the module is attached. The EM coils are fired by switching a gate, such as an SCR, by the signal processor embedded within the sensor module. After firing the coil, the capacitor is recharged by a DC-DC converter chip also located on the sensor module.

Advantageously, data acquisition performed by a sensor module is also controlled by its embedded processor. After receiving a command from the host CPU to acquire data, the embedded processor of the sensor module fires the EM coils and begins to sample an analog-to-digital converter (ADC) that is also located on the sensor module and which is input with signals from the feedback transducer(s). Analog time signals output by the embedded piezoelectric film transducer(s) are digitized by the ADC and stored in the processor's memory. Data is converted to the frequency domain via a Fast Fourier Transform as will be appreciated by those skilled in the art. Time and/or frequency domain signatures are then transmitted to the host CPU for signature pattern analysis.

Pattern recognition and signal classification techniques are used in sorting the signals from the sensors, classifying their sources and identifying their cause. These techniques are used to analyze the data from the sensors in the context of a pattern space comprising features which are indicative of specific faults such as cracks, corrosion, and the like. The features facilitate identification of the signals output by the sensors. In one embodiment, use of a single sensor and actuation means located on a panel enables one to determine the location and magnitude of a force or pressure applied to the panel.

A significant aspect of the monitoring system is the detection of significant changes in the modal parameters of the monitored structure. Time and/or frequency domain characteristics of a failure mode or of unsound members are identified by the monitoring system. Based on features such as measured frequency response, the modal frequencies, damping characteristics, mode shapes, peak energy, band-limited energy, total energy etc., vibration signatures and changes thereto can be correlated to specific structural defects. These features are sensitive indicators of changes that occur in physical properties of the monitored structure, such as changes in mass, damping and stiffness. The pattern recognition techniques employed train the system to interpret different types of signals without human intervention. Analyses of the sensor signals preferably includes the following operations: power spectral density determination, root-mean-square (RMS) averaging, and probability analyses as well as cross-correlation of the relevant signals. Spectral analyses techniques are employed to detect rivit line corrosion from structural modal signatures and discriminate corrosion from other structural defects such as cracks or strain.

The system undergoes a learning stage to extract and identify data and features which characterize the vibration signals, and to build up a database of statistics which describe the structure and various signals, especially for normal and steady-state operation. Properties and identifying information are derived from the features and various signals and are stored and compared with their unknown counterparts from the dynamic response of the structure which may be affected by any of a wide variety of factors such as ice accretion, fatigue cracks, corrosion, structural damage, etc. By analyzing their differences and similarities, the system identifies the nature of these signals, features, and what they represent. Marked discontinuities of key features of the vibration signal are used to identify structural abnormalities and the like. Accordingly, structurally sound members are distinguished from structurally unsound members.

As will be appreciated by one skilled in the art, an illustrative quantitative tool which can be used for comparing mode shapes is the Modal Assurance Criterion. This calculation, which is the squared magnitude of the DOT product between two complex unit vector arrays which define the mode shapes, results in a single number for comparing shapes; this single number will be one (1) if the shapes are identical to each other, and zero (0) if they are unlike one another. A mode shape is the geometric shape of the excited structure.

Mode shapes can be measured by the sensor modules from as many points on the structure as desired. As with time domain sampling of a signal, the more a mode shape is sampled, the more accurately a change can be pin-pointed to a specific region of the structure when a change in its mode shape is detected.

In another embodiment, thin film piezoelectric capacitive transducers can be applied directly onto an outer surface of an aircraft. This technique is especially appealing for retrofit of aircraft. Advantageously, such sensors also detect electrical continuity when used, for example, in parallel or series arrays. A crack in the aircraft skin disrupts the electrical path of the sensor and, in particular, changes total path capacitance and/or resistance of the circuit, signifying the presence of a fault. Advantageously, the sensors are configured to ensure against a single point failure, i.e., the system will not be totally disabled by a single fault.

The sensors of the invention provide continuous monitoring and reduce the need for at least some conventional periodic maintenance checks. Electronic measurement in accordance with the invention is more systematic and thorough than current inspection and operational checks. Cost-effective sensors and processors are employed to automate much of the inspection task. Computers integrated into instruments and programmed to analyze the complex interactions of aircraft structure provide real-time non-destructive evaluation in-flight. A profile of the entire structure is made quickly to pinpoint problems within minutes.

As part of a pre-flight check, the flight or maintenance crew can conduct a structural health scan employing an on board health monitoring computer. Such a scan will indicate evidence of stress and other disturbances as well as intensity and location of the stress. Comparison of the scan data with baseline measurements of structural components under controlled stress or under no applied stress determines if a structural component remains normal. An electronic database including results of numerous scans conducted during the operational life of the aircraft or its components charts the progressive toll of flight hours, takeoffs and landings. Periodic recordings are examined to reveal if the performance of structural member(s), such as connecting joints, rivit lines, mountings, skin or power plants show structural deterioration. This approach indicates whether an aircraft is safe after encountering conditions extreme enough to potentially affect performance yet not extreme enough to call for a full-scale strip-down of the aircraft.

Historical comparison of data might apply, for instance, to a military aircraft after strenuous flight maneuvers or to a commercial airliner after an emergency landing or buffeting by severe weather. Utilized for real time damage detection, the HMS system provides invaluable information on the integrity of the aircraft as it receives damage; such information can warn the pilot and enable corrective action to be taken, or prepare the pilot for the ultimate loss of the aircraft. This also applies to spacecraft when, for example, confronted with orbiting space debris or meteor damage.

BRIEF DESCRIPTION OF THE DRAWINGS

These and other objects, features and advantages of the present invention will become more readily apparent from the following detailed description of the invention in which like elements are labelled similarly and in which:

FIG. 10 depicts a sensor network suitable for detecting and monitoring fatigue cracks, strains and the like;

DETAILED DESCRIPTION OF THE DRAWINGS

The structural health monitoring system described herein may be implemented in two main configurations, a centralized configuration in which essentially all data processing is performed at a central location, including data acquisition and control; and a dispersed configuration where data acquisition and limited signal processing are performed at and by each individual remote sensor module. In the centralized system, relatively high voltage is generated from a single power source and transmitted over various lines and/or cables to the sensor modules, while in the dispersed system the high voltage power lines are eliminated by making use of microchip DC-DC power converters located at each of the remote sensor modules. The dispersed configuration is generally preferred, at least for relatively extensive monitoring systems and large structures, due to increased processing power and less restrictions relating to size, weight and power requirements.

Figure 1:
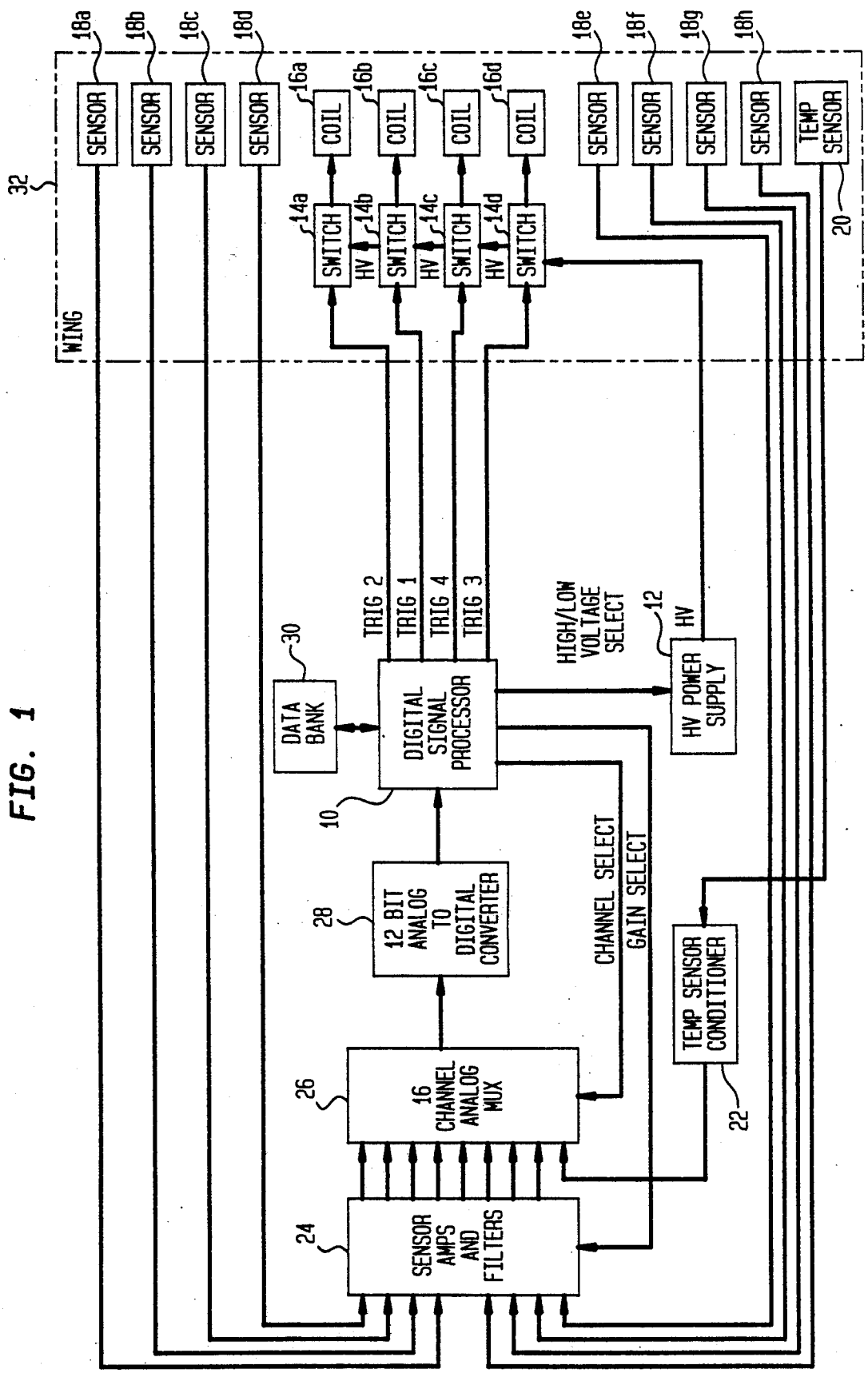
FIG. 1 is a block diagram of a centralized health monitoring system according to the present invention and having four actuators and eight independent sensors to monitor four separate areas of a structure.

FIG. 1 depicts a block diagram of the centralized configuration comprising a digital signal processor (DSP) 10, a high voltage power supply 12, switches 14a-14d electro-magnetic (EM) coils 16a-16d, vibration sensors 18a-18h, a temperature sensor 20, a temperature sensor conditioner 22, a filter 24, a multiplexer 26, analog-to-digital converter 28 and a memory storage device 30.

Digital signal processor 10 controls the system and is preferably an Intel 80386 microprocessor combined with an 80387 math co-processor. Processor 10 initiates a data acquisition cycle and triggers the high voltage power supply 12 by activating switches 14a-14d. Each of switches 14a-14d illustratively comprises a silicon controlled rectifier (SCR). Switches 14a-14d transmit energy stored in power supply 12 and provide such energy as an electrical impulse into coils 16a-16d. Application of such an impulse to each of coils 16a-16d provides a corresponding plurality of excitation forces to a monitored structure 32. Depending on the specific implementation, the coils may be fired simultaneously or sequentially. Vibration sensor 18a-18h (i.e., feedback transducers) are also located on structure 32 and respond to the vibration of the structure caused by the excitation forces. Sensors 18a-18h generate electrical signals corresponding to the vibration; these signals are amplified and filtered in filter 24. Illustratively, each of coils 16a-16d comprises a pair of coils separated by a pre-determined width on the order of a few mils. Multiple sensor signals output by the feedback transducers are selectively input through multiplexer 26 and digitized using analog-to-digital converter 28. The digitized data is then input to processor 10 and processed using software stored in memory 30. A signal from temperature sensor 20 is also read by the processor after being conditioned by filter 24. Temperature sensor 20 enables the processor to determine whether structural conditions are temperature dependent and whether icing conditions may exist. Use of four actuators and eight sensors is exemplary; any practical number of actuators and any practical number of sensors may be employed.

Figure 2:
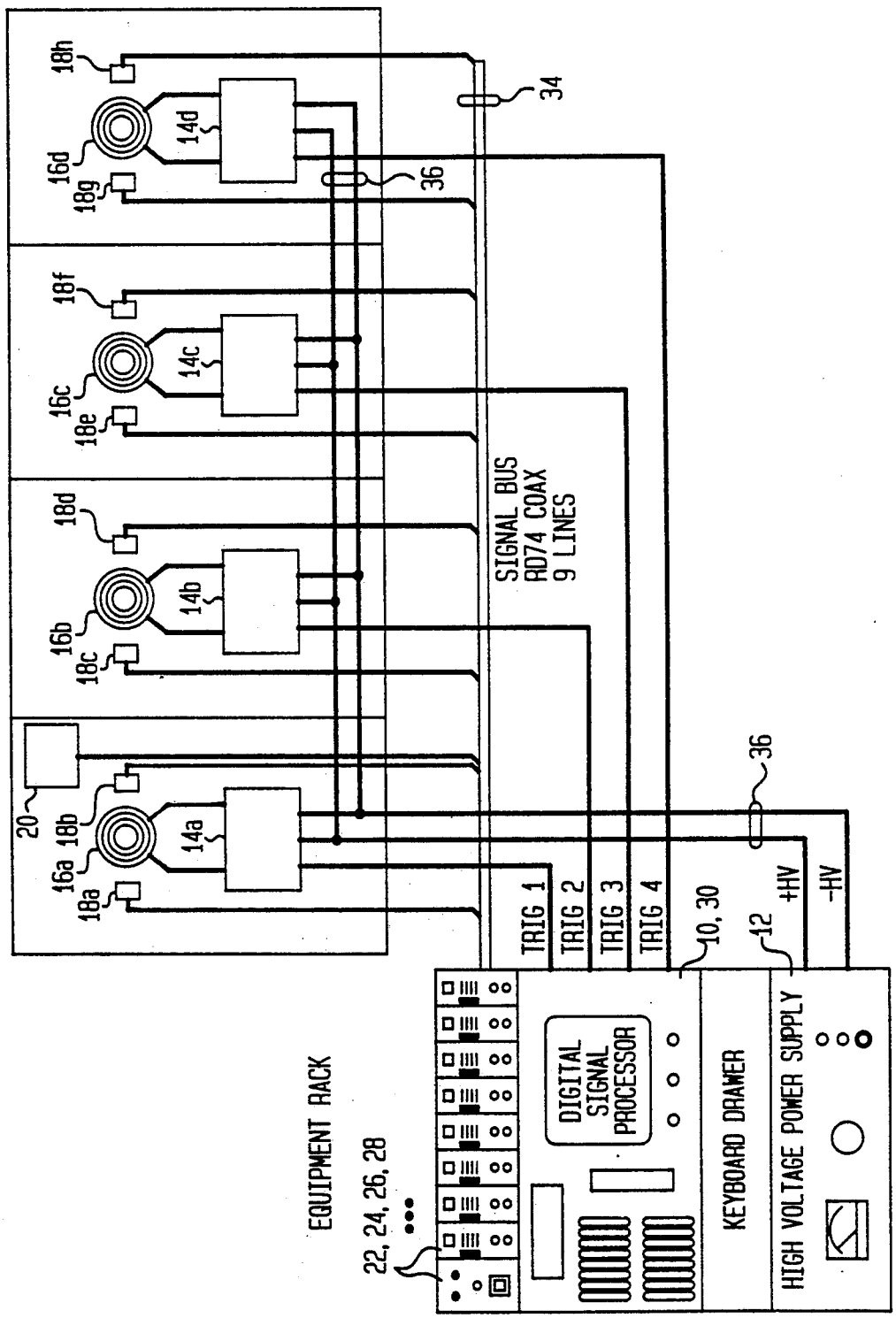
FIG. 2 depicts the centralized health monitoring system of FIG. 1 installed in an aircraft wing section.

An illustrative implementation of the centralized health monitoring system is shown in FIG. 2 and comprises the following key hardware elements: 1) a central processing module (CPM) comprising processor 10, power supply 12, conditioner 22, filter 24, multiplexer 26, converter 28 and memory 30; 2) feedback transducer 18a-18h 3) electromagnetic coils 16a-16d; 4) analog signal bus 34; and 5) high voltage power bus 36.

Illustratively, the CPM is a self contained 19" rack mounted unit having an IBM 80386 computer, high impedance sensor amplifiers, analog-to-digital converters, excitation actuator control electronics, temperature control circuitry, data storage unit, random access memory, and graphics display. The CPM is linked to an array of feedback transducers 18a-18h by way of analog signal bus 34. Feedback transducers 18a-18h are preferably piezoelectric sensors and are affixed to the wing structure 32. A data acquisition cycle is initiated by the CPM which triggers the electromagnetic coils which are firmly attached to the wing structure and which operate as actuators. Relatively high voltage is used by the coils to induce mechanical stresses on the structure. Such voltage is delivered to actuator coils 16a-16d by means of high voltage power bus 36. The coils are fired by switches 14a-14d. The resulting mechanical excitation of the structure is detected by sensors 18a-18h and processed using pattern recognition techniques. The CPM is configured to allow data from multiple sensors 18a-18h to be processed. In one illustrative embodiment, a total of 2086 samples are read from each sensor at a sampling rate of 20 kHz.

Sensors 18a-18h are preferably constructed from polyvinylidene fluoride (PVDF), a piezoelectric polymer. PVDF can be polarized by suitable processing during manufacture, i.e., it can be made piezoelectrically active. PVDF is an electrical insulator in its non-polarized form, but in its polarized form, PVDF is a relatively tough and flexible piezoelectric polymer. Polarized PVDF is commercially available as a thin polymeric film that generally has an ultrathin layer of nickel or aluminum deposited on each side to conduct a voltage across its faces. The PVDF sensors are physically sized to be integral with and easily attached to the structural members. Sensitivity is sufficient to obtain structural modal signatures using an impulse excitation source.

The PVDF sensor is based upon the piezoelectric properties of polyvinylidene fluoride. Piezoelectricity is a capability of certain crystalline materials to change their dimensions when subjected to an electrical field or, conversely, to produce electrical signals when mechanically deformed. When used as a sensor to sense deformation, the deformation produces an output voltage proportional to the dynamic strain applied over the film's area. PVDF has a broadband frequency response from near DC to over a megahertz enabling measurement of boundary layer forces and the like over a wide bandwidth.

Figure 3:
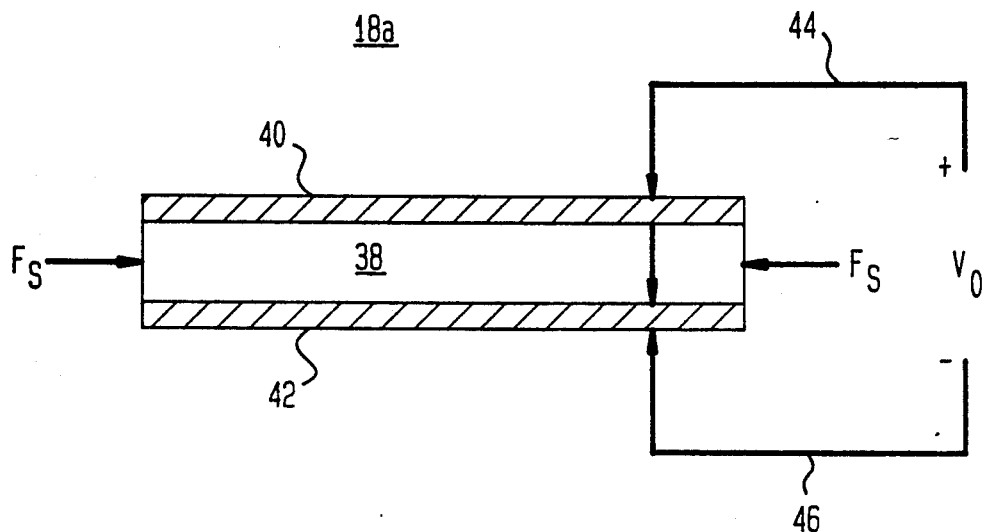
FIG. 3 depicts a single piezoelectric transducer polarized in a first direction and suitable for use as a transducer in the sensor module of the invention.

FIG. 3 depicts a single sensor 18a suitable for use as a dynamic strain sensor or feedback transducer in accordance with the present invention. Sensor 18a preferably is a polyvinylidene fluoride (PVDF) transducer film sensor comprising a polyvinylidene fluoride layer 38, a first low resistance contact 40 and a second low resistance contact 42. Conductive means 44 is attached to first low resistance contact 40 and conductive means 46 is attached to second low resistance contact 42. Illustratively, low resistance contacts 40, 42 are each metallization layers deposited or etched by conventional methods onto PVDF layer 38 such as aluminum or nickel metallization layers. Advantageously, layers 40, 42 may be patterned, such as by employing etching techniques, to yield a plurality of sensors associated with a single PVDF layer.

As will be appreciated by one skilled in the art, sensor 18a has a certain amount of capacitance and may operate as a capacitor having a capacitance determined by the dielectric constant of PVDF layer 38, the area of metallization layers 40 and 42 and the thickness of PVDF layer 38 separating metallization layers 40 and 42.

The PVDF sensor 18a depicted in FIG. 3 has its PVDF layer 38 polarized in a direction so as to produce an output voltage $V_o$ across metallization layers 40, 42 upon the application of a force in a shear direction as indicated by the arrows $F_s$. In other words, PVDF sensor 18a is polarized in a direction so as to be especially sensitive to application of force in the $F_s$ direction.

Figure 4:
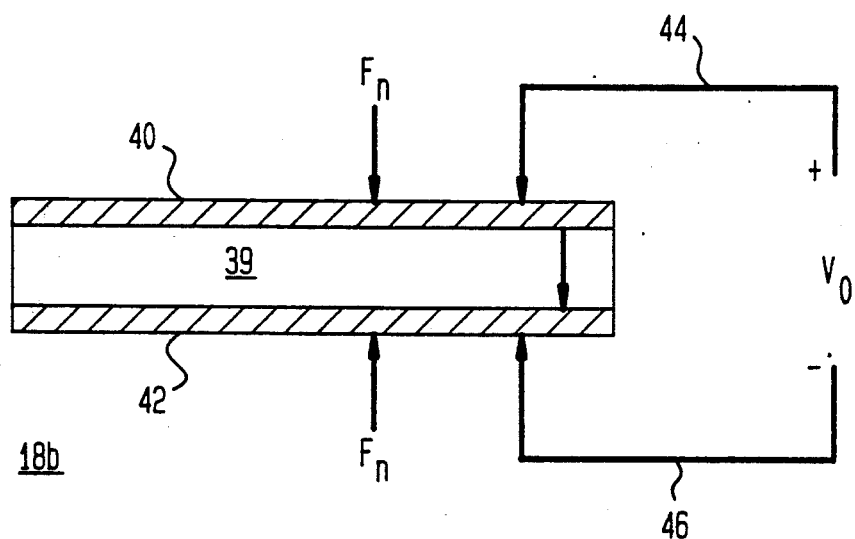
FIG. 4 depicts a single piezoelectric transducer polarized in a second direction and suitable for use as a transducer in the sensor module of the invention.

The PVDF sensor 18b depicted in FIG. 4 has its PVDF layer 39 polarized in a direction so as to produce an output voltage $V_o$ of increased magnitude across metallization layers 40, 42 upon the application of a force in a normal direction as indicated by the arrows $F_n$. Accordingly, sensor 18b of FIG. 4 is especially sensitive to application of force in the $F_n$ direction. Advantageously, sensors 18a-18h of FIGS. 1, 2 may comprise sensors of the type depicted in FIG. 3 as well as those depicted in FIG. 4.

Figure 5:
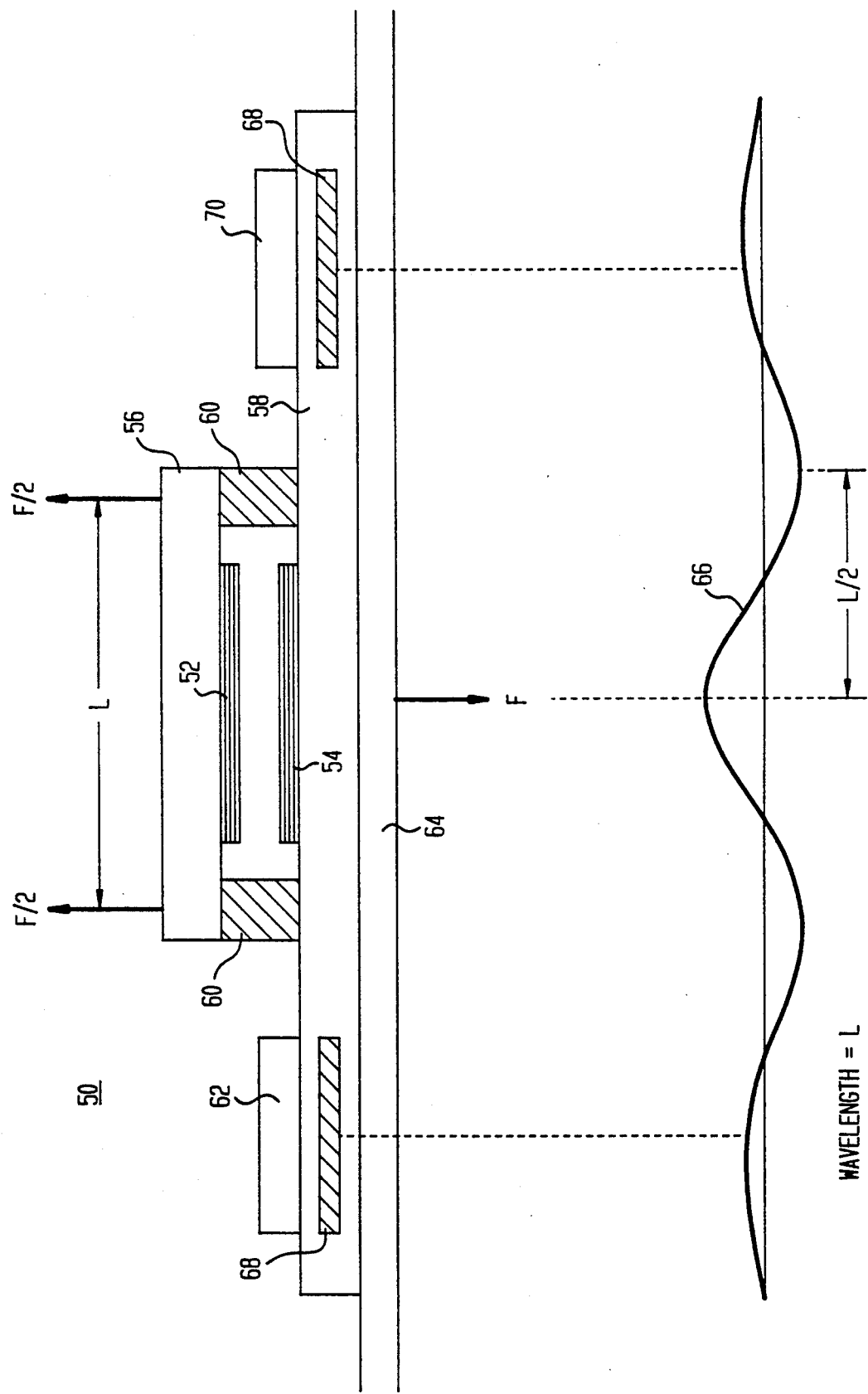
FIG. 5 schematically depicts an illustrative sensor module for use in a dispersed health monitoring system and a surface wave resulting from actuation of the module.

FIG. 5 schematically depicts an illustrative embodiment of a sensor module 50 for use in the dispersed health monitoring system of the present invention.

Sensor module 50 comprises a pair of coils 52, 54 which are etched on printed circuit boards 56, 58, respectively, and separated from each other by a resilient flex joint 60. Joint 60 may comprise an annular ring or two parallel spaced-apart strips or any of a wide variety of geometrical shapes or combination of such shapes.

An energy storage unit 62, illustratively a 100 μF capacitor having a 100 microsecond capacitor discharge pulse is employed to fire the coils. Some implementations of the invention may require physically small capacitors. Accordingly, such implementations will employ capacitors having capacitance values less than 100 μF, since smaller values of capacitance will result in physically smaller capacitors. As will be appreciated by one skilled in the art, the rapid collapse of the electromagnetic field generated by firing the two coils creates a sharp impulse force (depicted as arrow "F") that is transmitted to structure 64. Reactive forces (depicted as two arrows "F/2") are also transmitted to structure 64 through flex joints 60 to create a surface wave 66 of wavelength L. The wavelength, L, is twice he distance separating the point where the sharp impulses force is applied and the point where an average force of the reactive forces is applied. Advantageously, by properly selecting input signal pulsewidth and the geometric physical parameter L, this push-pull technique is used to influence bandlimited vibration in the structure. Embedded sensors 68 are preferably of the type depicted in FIGS. 3 and 4. Embedded sensors 68 detect the resultant structural vibration and generate corresponding electrical signals as described in conjunction with FIGS. 1–4. These electrical signals are amplified and processed by signal processing circuitry 70. This design enables the actuator formed by coils 52, 54 to be used on metallic (e.g., aluminum) as well as composite structures. By suitably selecting parameters such as L, capacitance, capacitor discharge impulse voltage, current and duration, desired wave shaping can be accomplished as shown in FIG. 5.

Figure 6:
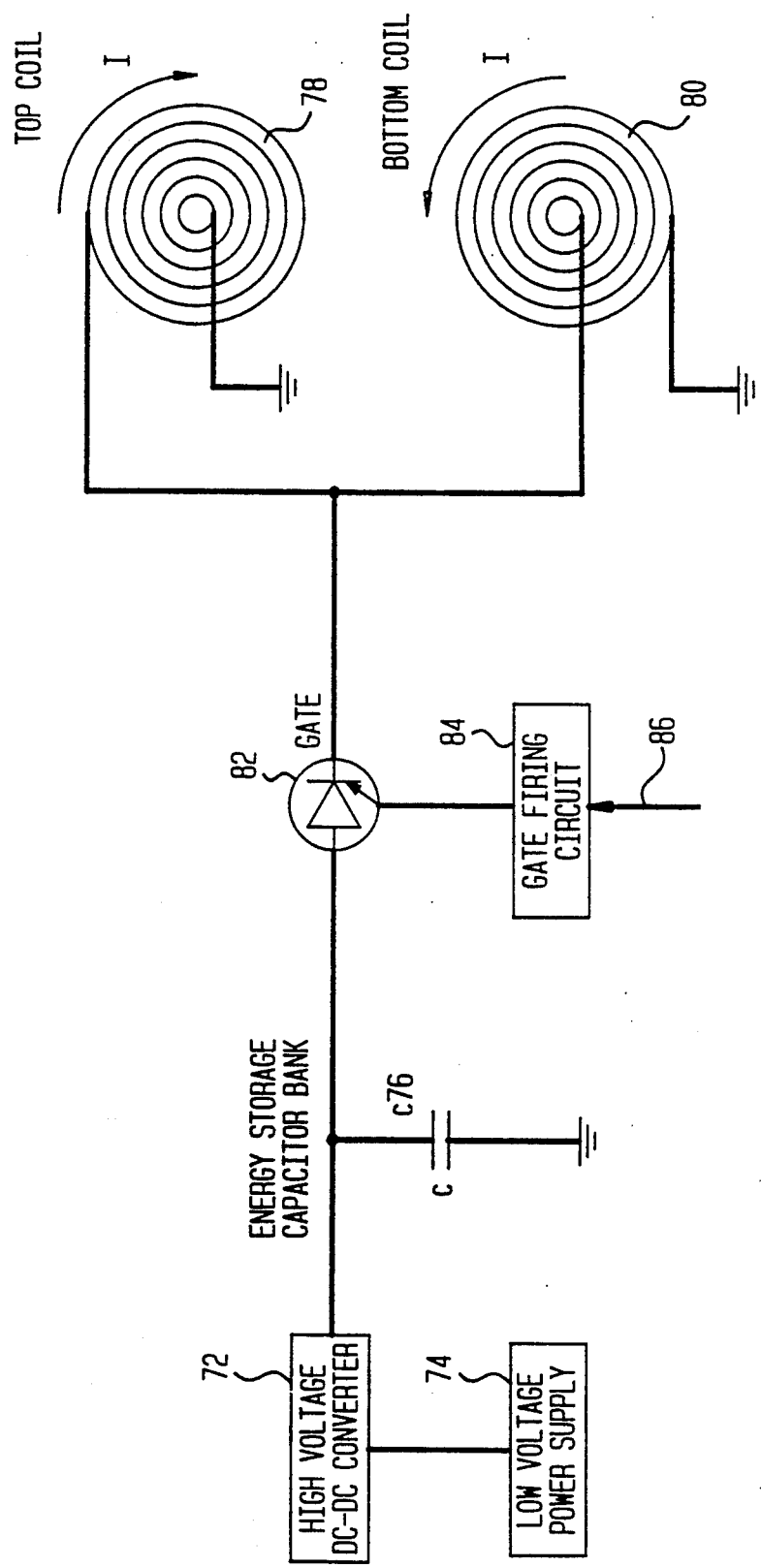
FIG. 6 is a block diagram of an electro-magnetic coil charging and firing circuit.

FIG. 6 depicts a block diagram of the actuator charging and firing circuit. High voltage is generated by a DC-DC converter 72 powered by a low voltage power supply 74. Advantageously, such use of a DC-DC converter eliminates the need for a high voltage bus. Converter 72 charges capacitor C76 to the desired threshold excitation voltage, which depends on numerous factors, including the nature of the structure to be monitored. Excitation voltages on the order of 100–400 volts are suitable for some embodiments. The stored capacitive energy is discharged to actuator coils 78 and 80 by a high current gate 82, preferably a silicon controlled rectifier. Actuator coils 78 and 80 may be, for example, circular in shape. The gate is activated by a firing circuit 84 that provides electrical isolation from an input signal generated by the digital processor and transmitted over line 86 to circuit 84. As will be appreciated by one skilled in the art, application of current of opposite polarity to the two coils, as shown in FIG. 6, provides an impulse force.

Figure 7:
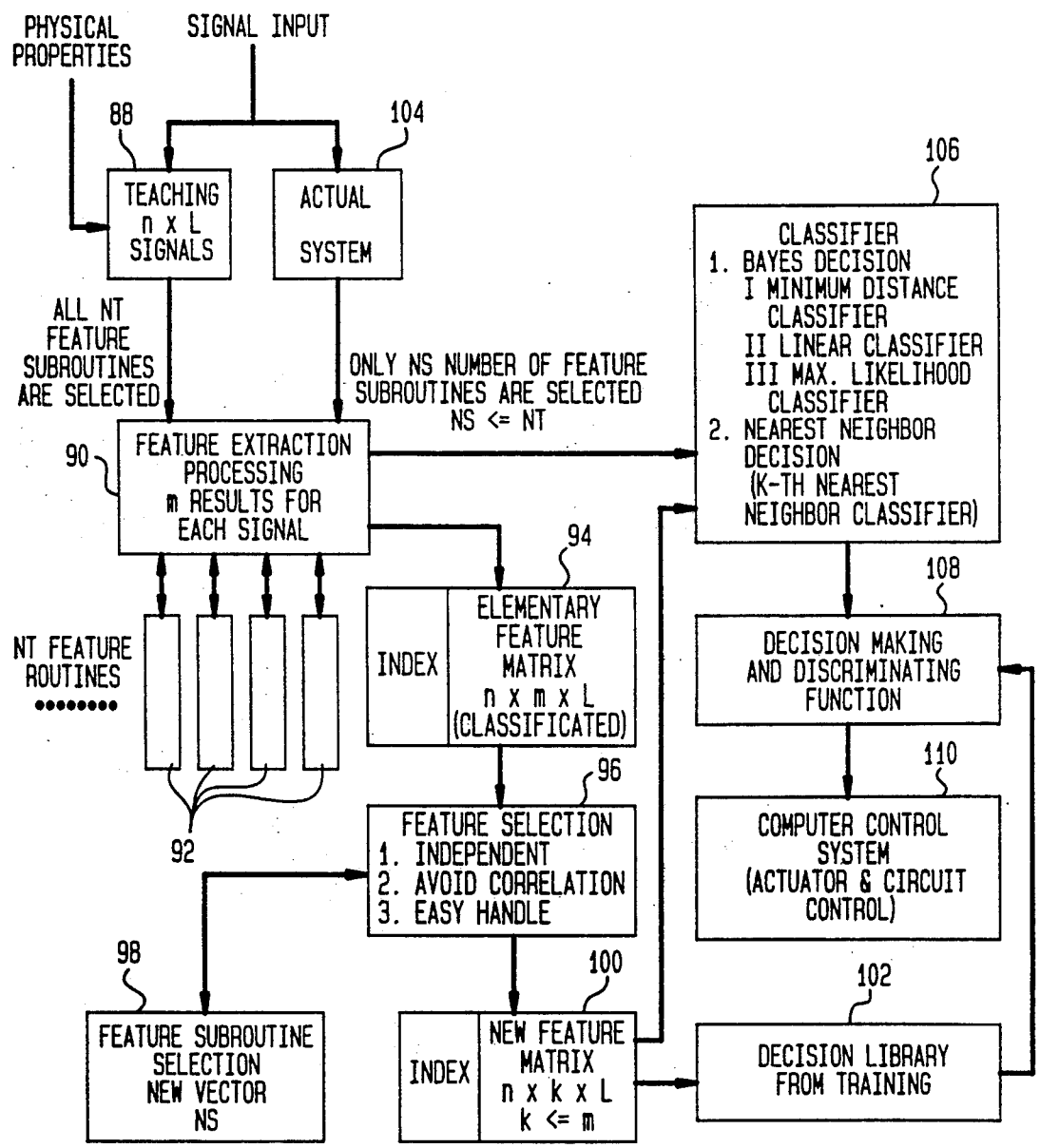
FIG. 7 is a flowchart of a pattern recognition based software algorithm for distinguishing among characteristics relating to fatigue, corrosion, ice accretion, etc.

Pattern recognition and signal classification techniques are preferably used for identifying and sorting the signals and for classifying the type and location of damage or disturbance. A flow chart of suitable pattern recognition software is shown in FIG. 7. The system first goes through a learning stage to establish baseline measurements and responses of the system. Specifically, experimental data is initially input into a training routine (88). A feature processor (90) extracts feature vectors computed in subroutines (92) and builds up statistics which describe various signals. The patterns generated from the feature extraction process consist of features that describe the vibration signals. These features include both time and frequency domain parameters.

Twenty-five illustrative features employed in one embodiment of the invention are identified as follows:

LIST OF FEATURES

1. Amplitude Ratio (AR) is defined as the ratio of the second largest peak amplitude to the largest peak amplitude in the power spectrum:

$$AR = P2/P1$$

where
P1 = Power of the largest peak amplitude,
P2 = Power of the second largest peak amplitude.

2. The frequency of the largest peak amplitude.
3. The frequency difference of the first largest peak amplitude and the second largest peak amplitude.
4. Partial energy in the frequency band 100 Hz to 700 Hz. Partial energy from frequency w1 to w2 is defined as:

$$\Delta E = \int_{w1}^{w2} \frac{1}{2\pi} |F(\omega)|^2 \, d\omega$$

5. Partial energy in the frequency band 0.7 to 2.65 KHz.
6. Partial energy in the frequency band 2.65 to 7.0 KHz.
7. Ratio of the smallest partial energy to the largest partial energy.
8. Number of power spectrum density (PSD) peaks exceeding a given threshold.
9. The frequency at which 25% of the total energy is observed. Total energy is defined as:

$$\Sigma = \frac{1}{2\pi} \int_{-\infty}^{\infty} |F(\omega)|^2 \, d\omega$$

10. The frequency at which 50% of the total energy is observed.
11. The frequency at which 75% of the total energy is observed.
12-19. Eight local damping numbers:

$$\xi_\iota = \frac{\delta_\iota}{\sqrt{4\pi^2 + \delta_\iota^2}} \text{ where } \delta_\iota = [X(\iota + 1)]/X\iota, \iota = 1, \ldots 8$$

20. One half of the demodulation period, Tm.
21. Standard deviation of the signal, $\sigma$:

$$\sigma(x1, \ldots xn) = (Var(x1, \ldots xn))^{\frac{1}{2}}$$

$$Var(x1, \ldots xn) = 1/N - 1 \sum_{j=1}^{N} (xj - x)^2$$

22. Kurtosis of the signal, Ku. Ku is the ratio of the fourth moment to the square of the second moment:

$$Ku = M4/(M2)^2 \text{ where } Mn = \int_0^\infty t^n f(t) dt$$

Skewness of the signal, Sk. Sk is the ratio of the third moment to the 1.5 power of the second moment:

$$Sk = M3/(M2)^{1.5}$$

24. The time for 90% of the signal to decay, Td.
25. Ratio of partial energy of a first sensor to partial energy of a second sensor.

The physical properties which describe the various signals are then tagged to each corresponding feature vector. Once the system is trained, an elementary feature matrix is formed (94). For the features listed in the above List of Features, the elementary feature matrix comprises twenty-five numbers. A feature optimization routine (96) then performs an analysis of the ability of individual features to distinguish between various signal types and classes. This analysis includes histogram and correlation processing (98). A new feature matrix is then computed in a routine (100) and stored in a decision library (102). After training, the system is ready for testing. Signal data is input into a testing routine (104) and selected features are extracted. Signal classification (106) is made on the basis of the pattern features selected, and employs the distance between the features of the input measurement pattern and a reference in the vector space. Signal classification (106) may select the pattern features from the new feature matrix computed in the routine (100).

During signal classification, an input datum is assigned to one of the reference patterns, which is associated with the closest vector. Input data is identified with the class or type of its nearest neighbor, where nearness is preferably measured by Euclidean distance. A decision routine (108) then determines the signal type and, based on the results, sends a command signal to an actuator control routine (110). The decision routine (108) utilizes the new feature matrix stored in the decision library (102).

Various features which can be used for characterizing failure modes are empirically determined. These features are preferably based on the modal frequency response of the structural member. Key features are determined which are most useful in describing the vibration signals as they change in response to any structural degradation or the like.

Vibration experiments are performed to generate a database with and without data corresponding to damaged members in order to "train" the damage detection software. The pattern feature set is preferably generated and optimized using histogram analysis. Once the software has been trained, the system is then tested under various damage conditions to demonstrate and evaluate the damage detection method.

Figure 8:
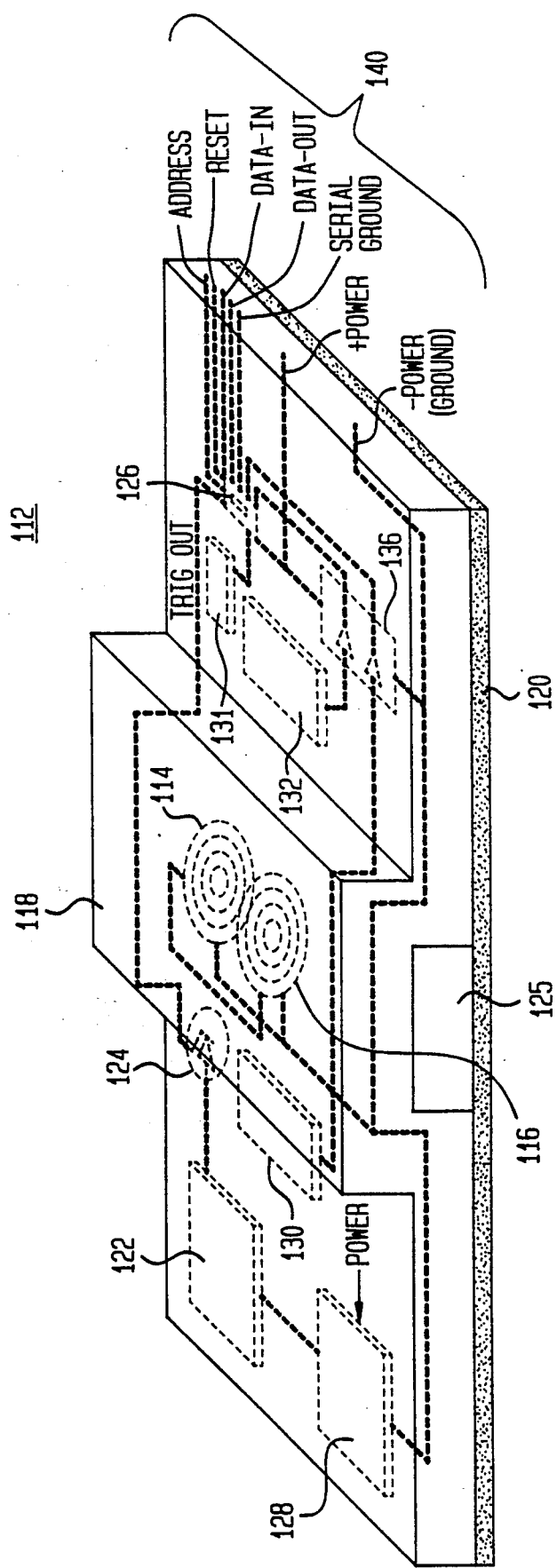
FIG. 8 depicts a preferred sensor module with integral piezoelectric transducers, electromagnetic actuation coils, a coil firing circuit, a power converter/energy storage device, a signal conditioning circuit, and data acquisition and signal processing circuitry.

FIG. 8 depicts a preferred embodiment of a sensor module 112 for use in the dispersed health monitoring system of the present invention. Sensor module 112 comprises a pair of actuation coils 114, 116. Actuation coil 114 is the top actuation coil and is constructed by suitably etching copper on a top fiberglass printed circuit (PC) board 118. Actuation coil 116 is the bottom actuation coil and is constructed by suitably etching copper on a bottom PC board 120. Sensor module 112 also comprises energy storage means 122, such as a capacitor, a gate 124 such as an SCR, a signal processor 126, a DC-DC converter 128, sensors 130, 132, memory device 134, and amplifier/conditioner circuit 136. Sensors 130, 132 are preferably of the type depicted in FIGS. 3, 4.

The sensor module's actuation mechanism creates a physical impulse force by rapidly discharging energy storage capacitor 122 into the pair of opposed electromagnetic (EM) coils 114, 116 as described in FIGS. 5, 6. The coils are separated by a gap 125 (most clearly seen in FIG. 5) that widens when the current induced EM force field is applied, thus transmitting an impulse force to the structural member to which bottom PC board 120 is attached. In the resting state of the coils, this gap is only a few mils wide. The coils are fired by switching gate 124, illustratively an SCR. Signal processor 126 switches gate 124 and is embedded within the sensor module. After discharging into the coils, capacitor 122 is recharged by DC-DC converter 128 also located on the PC board.

Advantageously, data acquisition performed by the sensor module is controlled by embedded processor 126. This processor is preferably an Intel 83C522, an Intel 80386, or a TI 32000 series integrated circuit. After receiving a command from a host CPU (not shown) to acquire data, processor 126 fires EM coils 114, 116 by applying a signal to gate 124 over the "TRIG OUT" line. The coils then generate and apply a force to the structure, which is detected and transduced into analog electrical signals by sensors 130, 132. The analog time signals detected by the embedded piezoelectric film transducers 130, 132 are amplified, filtered and digitized in amplifier/conditioner circuit 136 which includes an ADC. Processor 126 then samples and stores the digitized data in memory device 134. Data is converted to the frequency domain via a Fast Fourier Transform as recognized by those skilled in the art. Time and/or frequency domain signatures are then transmitted to the central onboard computer for signature pattern analysis.

Figure 9:
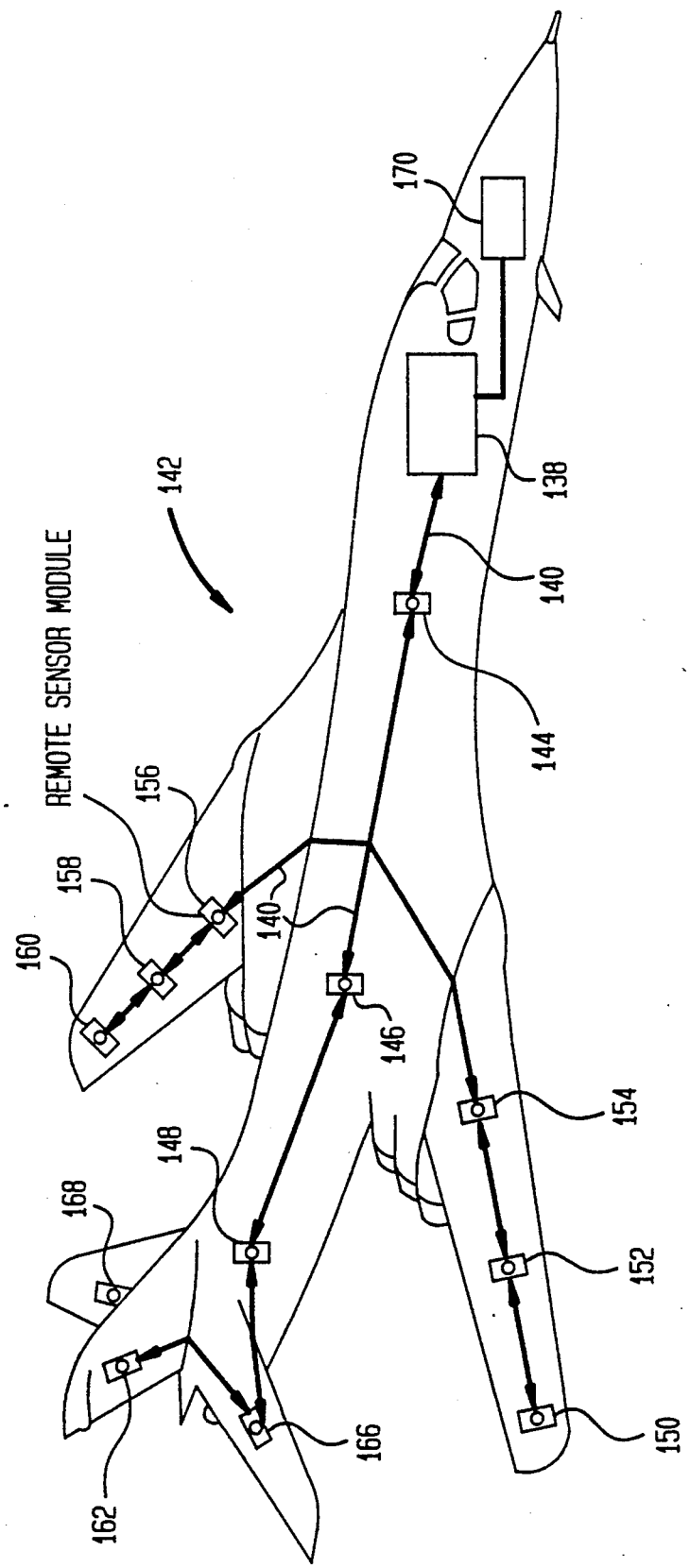
FIG. 9 depicts a typical aircraft equipped with a dispersed health monitoring system including sensor modules, a central processing and display module, and a data/power bus which is routed through the aircraft.

Each of a plurality of sensor modules 112 is interfaced to a central onboard computer 138 over a digital signal bus 140 as illustrated in FIGS. 8, 9. Bus 140 illustratively includes lines for power, power ground, serial-in communication, serial-out communication, serial ground, as well as a reset line and an address line. Computer 138 uses the address line to activate the sensor modules to a listening mode; computer 138 then transmits the desired module address code over the serial-in communication line. Upon receiving the proper address code, the desired module is activated and initiates a data acquisition cycle. The coils are actuated and sensor signals are acquired, amplified, conditioned, digitized, and processed by processor 126, and then transmitted back to central computer 138 over the serial-out communication line. All transmitted data signals are referenced to the serial ground line of bus 140. Central computer 138 samples all modules preferably sequentially to conduct a health scan of the complete monitored structure. In the event of a module failure and subsequent bus tie-up, central computer 138 issues a reset pulse over the reset line and disables the failed module. The power line is also included in bus 140 to provide low voltage power required to operate sensor modules.

Specifically, FIG. 9 depicts an aircraft health monitoring system incorporating certain aspects of the present invention. In particular, an aircraft 142 is provided with fuselage sensors 144, 146, and 148, leading edge and top wing sensors 150, 152, 154, 156, 158, 160, tail sensors 162, 164 (only 162 shown) and horizontal stabilizer sensors 166, 168 The sensor modules are connected to onboard central computer 138 over signal bus 140. Data is acquired and processed for structural health status and displayed to the pilots or maintenance crew on monitor 170.

Figure 10:
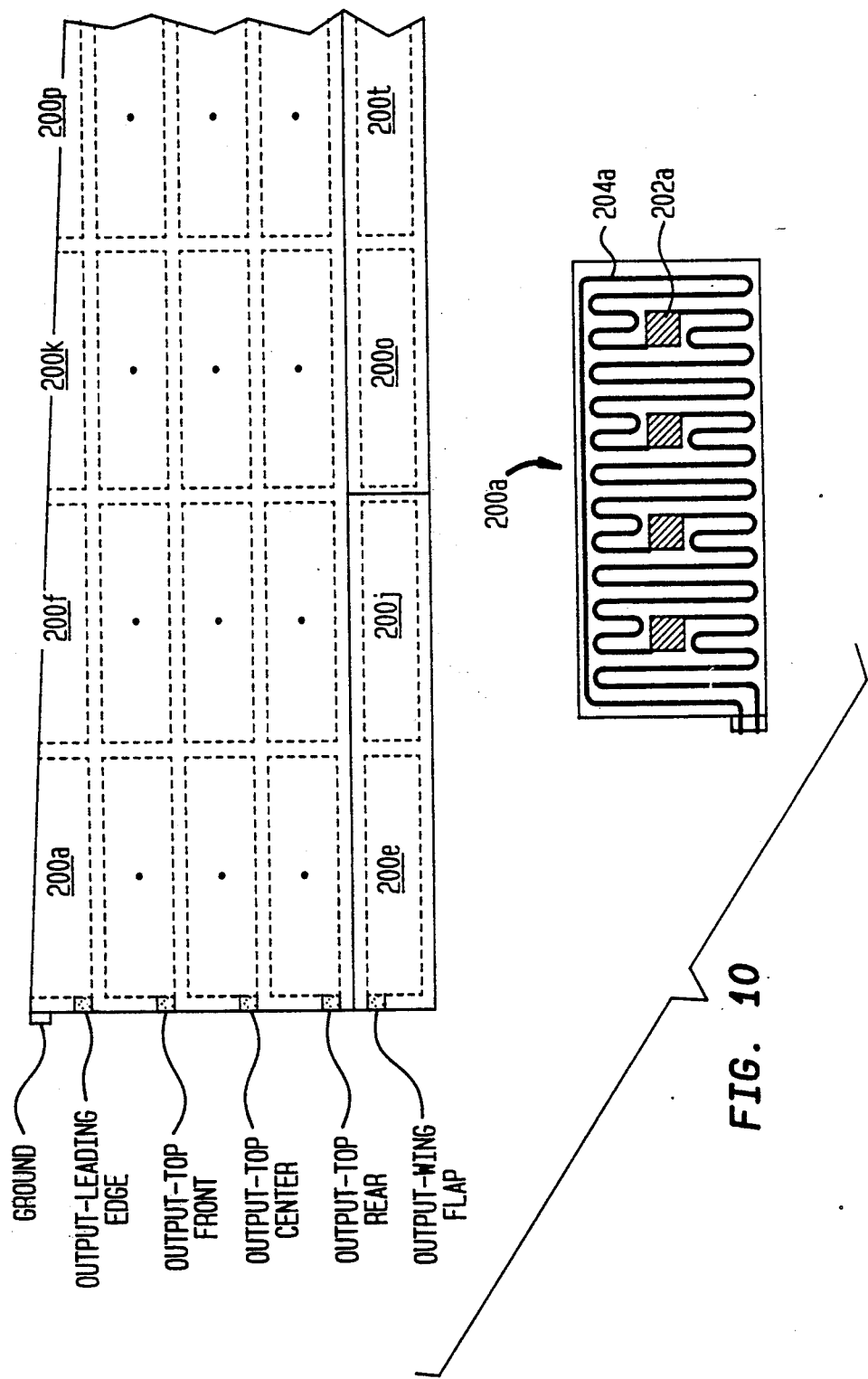

FIG. 10 depicts a sensor network suitable for detecting and monitoring fatigue cracks, strain and the like. This sensor network includes a plurality of sensor 200a-200t, each including at least one polarized PVDF sensor 202 preferably operating as a dynamic strain sensor and at least one capacitance/continuity sensor 204 preferably operating as a fatigue crack locator. In this embodiment, each of sensors 202 and 204 are connected in series, although in other embodiments various combinations of sensors 202 and 204 may be connected in parallel.

Sensor 202 is preferably a polarized PVDF capacitive sensor and sensor 204 is preferably the metallization pattern etched on the PVDF film which also forms one electrode of sensor 202. In order to enable intelligent interpretation and analysis of detected and monitored signals, and in order to better pinpoint the location of faults, each of sensor arrays 200a-200t preferably provides a separate input to a central computer system.

In particular, sensor 204 of each of sensor arrays 200a-200t comprises thin metallization paths etched on a first or upper surface of the PVDF film which forms polarized active element 202. The metallization path is firmly attached to but electrically insulated from the structure which it is to monitor. In this embodiment, the metallization path of sensor 204 is electrically insulated from the structure which it is to monitor by the remainder of PVDF sensor 202, which may include a second metallization layer on the opposite side of the PVDF layer. Alternatively, such a second layer is not necessary, especially if the structure is metallic since the metallic structure can serve as one electrode of a capacitor while sensor 204 serves as the other electrode and the PVDF layer of sensor 202 serves as the dielectric material. In the event that a crack is formed, the layout of the metallization path maximizes the likelihood that the path will cross the crack. The metallization path is firmly attached, via the PVDF layer, along its entire length to the structure which it is to monitor and is sufficiently thin and non-elastic such that the separation of the structure due to formation of a crack causes the metallization path to break and an open circuit to form. Accordingly, total path capacitance changes and responsive action may then be taken.

Sensor 202a preferably comprises the metallization layer or path of sensor 200a in FIG. 10 and the PVDF layer attached to and located behind the depicted metallization layer. Continuity sensor 204a forms part of this metallization path of sensor 202a. This metallization path functions as a first electrode of 202a. Sensor 202a also includes a second electrode comprising a metallization layer (not shown) on a side of the PVDF film opposite the first electrode. This second electrode may cover the entire side of the PVDF film or may be approximately the same size as the first electrode and located across from the first electrode. Alternatively, the PVDF film may not be supplied with a second metallization layer, rather, the second metallization would be the metallic aircraft skin upon which the PVDF film is mounted. Dynamic strain measurements are obtained in accordance with the invention for the structural member to which sensor 202a is attached and can be processed employing the pattern recognition techniques described in FIG. 7. Specifically, physical changes to the structural member such as bending result in a similar physical change to sensor 202a, as well as sensor 204a. By monitoring the output of these sensors, the physical change can be detected. As will be appreciated, several sensors such as sensor 202a and/or 204a may be connected in series and the total capacitance measured.

As depicted in FIG. 10, an entire wing may be monitored for fatigue and crack detection. Alternatively, selected portions of an aircraft may be monitored with any of sensors 202, sensors 204 or both.

Figure 11:
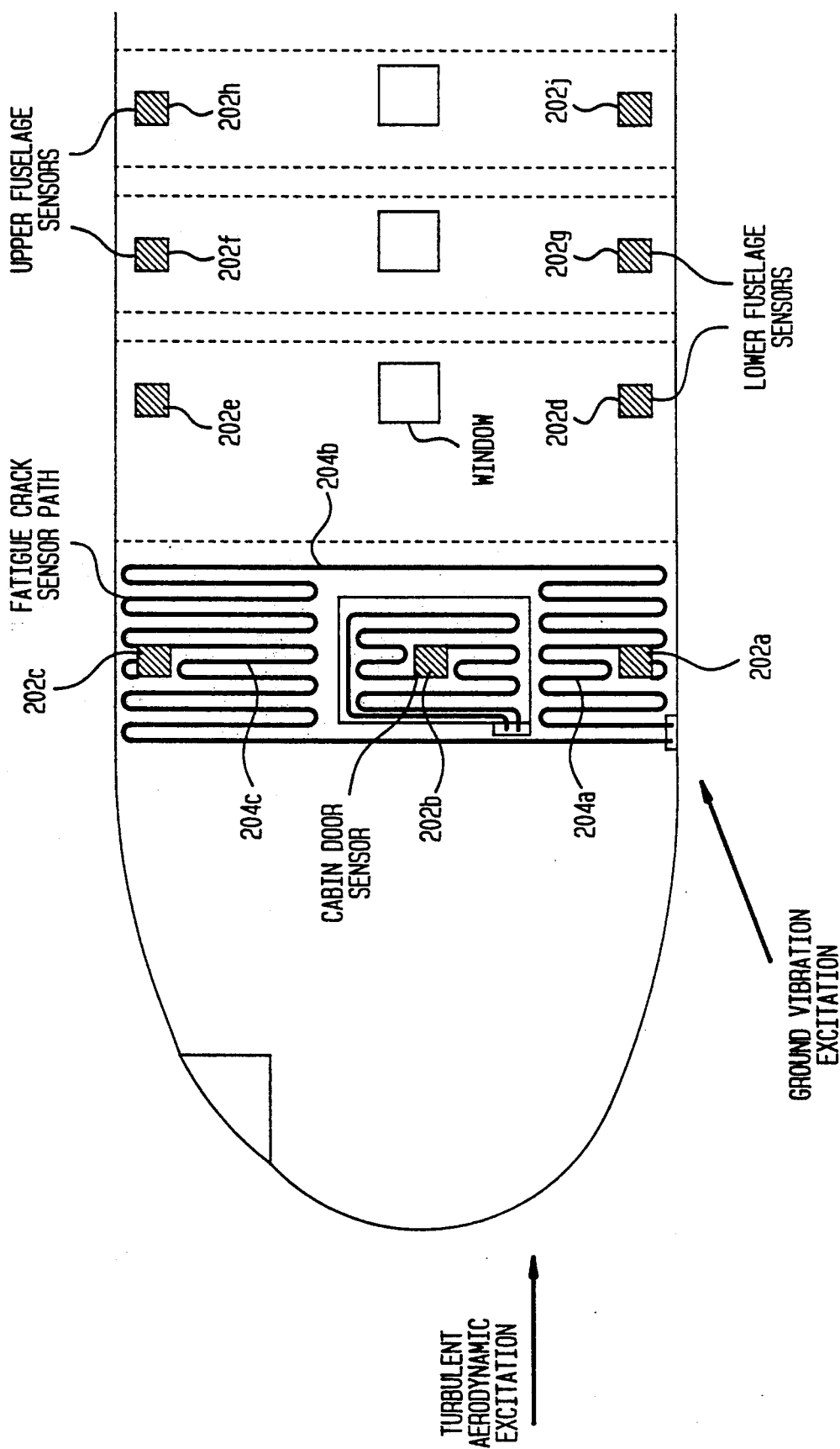
FIG. 11 depicts dynamic strain sensors and fatigue crack locators strategically placed on selected portions of an aircraft fuselage.

For example, and as depicted in FIG. 11, dynamic strain sensors 202a–202i as well as fatigue crack locators 204a–204i may be strategically placed on selected portions of the fuselage. For example, the cabin door as well as a forward section of the fuselage may be fitted with dynamic strain sensors and fatigue crack locators.

Figure 12:
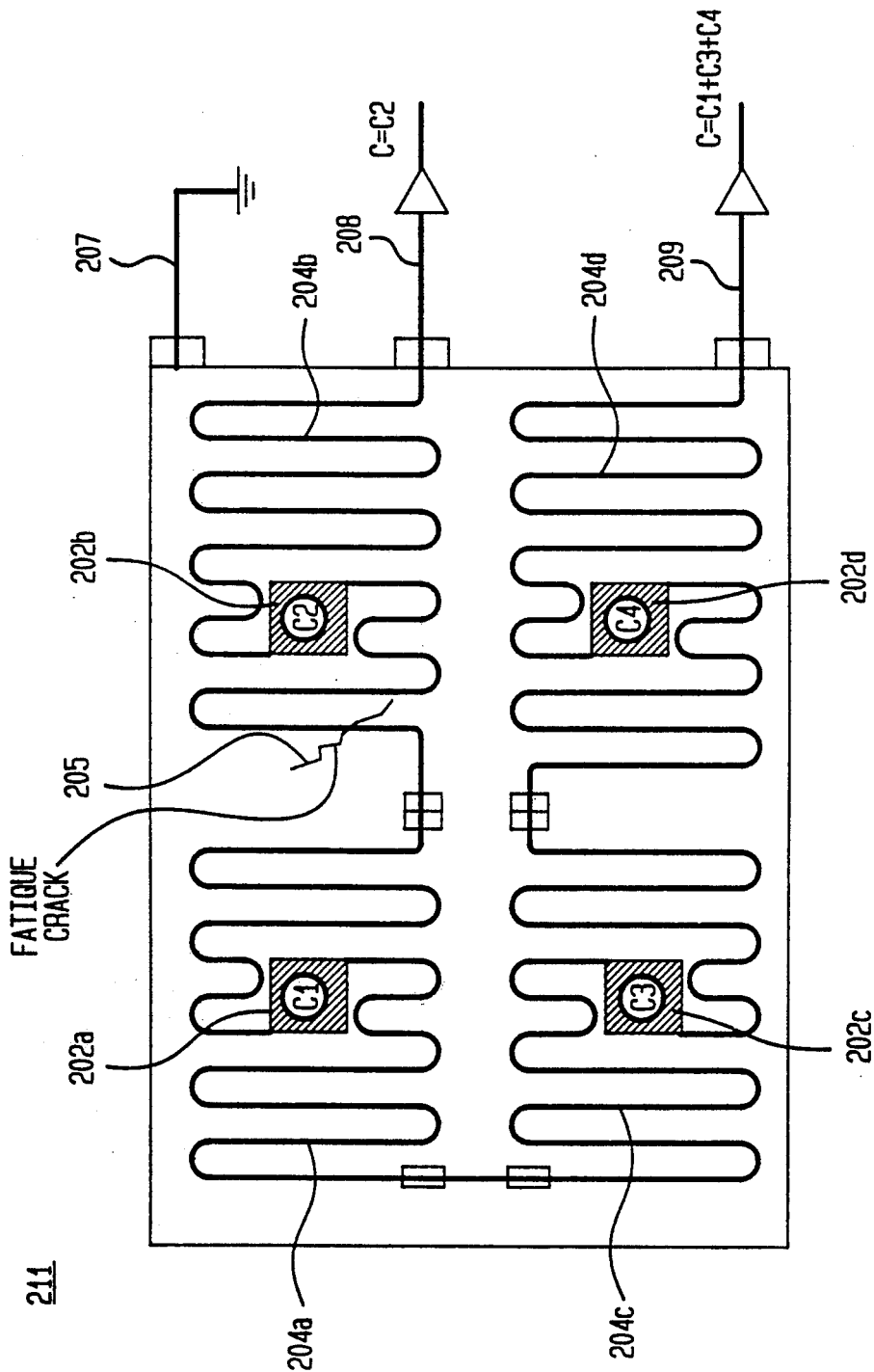
FIG. 12 depicts a sensor array which is not disabled by a single point failure due to a fatigue crack.

FIG. 12 depicts a sensor array 211 which is not disabled by a single point failure due to a fatigue crack 205. In particular, sensor array 211 comprises a plurality of dynamic strain sensors 202a–202d and a plurality of fatigue crack locators 204a–204d. Sensors 202a–202d, 204a–204d of FIG. 12 are similar in structure and function to sensors 202, 204 of FIGS. 10 and 11 The four sensors 202a–202d depicted in FIG. 12 have capacitance values C1, C2, C3, C4, respectively. Each of these capacitors comprises two electrodes separated by a PVDF layer. The four shaded boxes labelled Cl, C2, C3 and C4 form one electrode of each of the capacitors on one side of the PVDF layer and are preferably etched on the PVDF layer along with paths 204a–204d. The metallization layer (not shown) on the other side of the PVDF layer forms the other electrode which preferably is common to each of the four sensors 202a–202d around 207. Alternatively, the metallization layer may be etched so as to form four electrodes having the same shape and configuration as shaded boxes C1, C2, C3 and C4. Advantageously, should a fatigue crack 205 occur as indicated, output 208 of sensor 211 will be measured to have a capacitance (with respect to ground 207) equal to that of C2, and output 209 will be measured to have a capacitance (also with respect to ground 207) equal to the sum of the capacitance of C1, C2, C3 and C4. Thus, the location of the crack will be known to be between C2 and C1 and remedial action may be taken.

Figure 13:
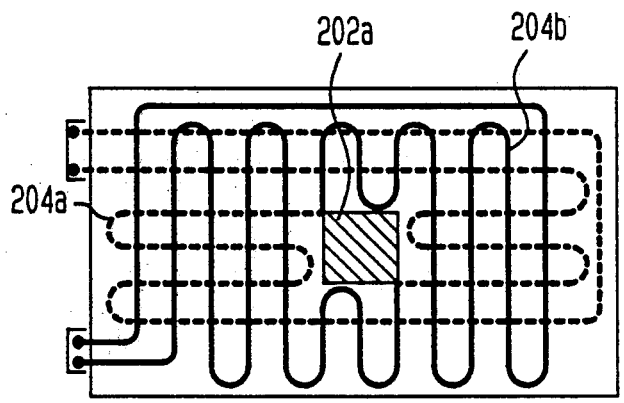
FIGS. 13-15 depict various configurations of dynamic strain sensors and fatigue crack locators.
Figure 14:
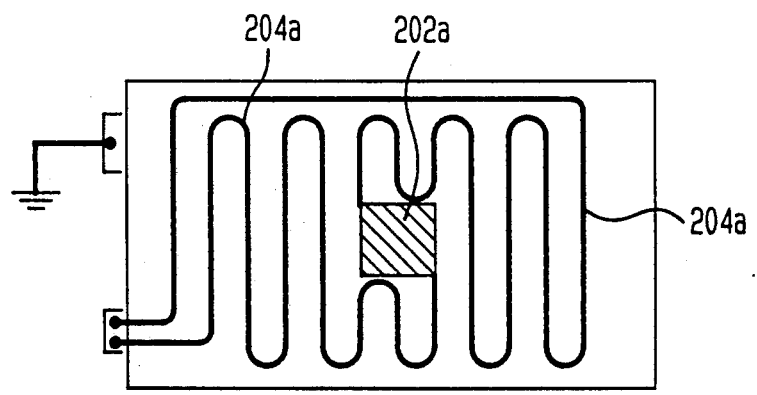
Figure 15:
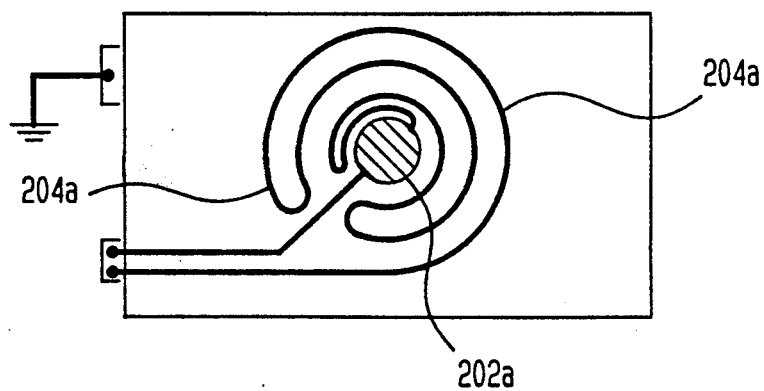

FIGS. 13–15 depict various configurations of sensors 202a–202d, 204a–204d. For example, FIG. 13 depicts dynamic strain sensor 202 and two fatigue crack locators 204a–204b in a grid format. This configuration may be applied to metals or to composite surfaces and has excellent area resolution for detecting cracks. The configurations depicted in FIGS. 14 and 15 employ a uniform base ground plane and are particularly useful for aluminum skinned aircraft that have an existing ground plane which serves as an electrode. Accordingly, the PVDF film of this embodiment is provided with only one metallization layer forming sensor 204a and one electrode of sensor 202a. These configurations also are well adapted to having a patterned metallization path, i.e., sensor 204a, formed on the PVDF layer.

Each of the sensors depicted in FIGS. 10–15 are preferably etched on a PVDF film, illustratively 10–110 um thick, with an active polarized element located therein. The active polarized element provides strain sensing capability as well as a reference capacitance value for fatigue crack monitoring. By polarizing the material, an input strain produces an output voltage as described in conjunction with FIGS. 3–4. While a first metallization layer is preferably etched on the PVDF film, a second metallization layer can be etched on an opposite side of the PVDF film or can comprise a metallic structure to which the PVDF layer is attached. Dynamic strain frequency response of the PVDF sensor extends from near DC to over a megahertz, whereas conventional strain gauges are only operable to a few kilohertz. Accordingly, suitably mounted sensors in accordance with this invention can monitor structural vibrations and frequencies for use as input to a HMS in accordance with the present invention.

Corrosion is detected in a manner similar to detection of strain and fatigue cracks. Specifically, corrosion is accompanied by a change in the signature of the monitored member such as that due to changes in material stiffness and damping. Rivit line corrosion can also cause significant variation in the boundary conditions of a structural member which alter modal frequencies and damping. Accordingly, the sensors of FIGS. 10–15 may be employed in the detection of corrosion by monitoring their output and employing the pattern recognition techniques described in FIG. 7.

More specifically, the sensors depicted in FIGS. 10–15 are preferably electronically scanned in real-time to determine conductor path integrity (i.e. path capacitance and resistance) and modal response indicative of material degradation using pattern recognition techniques described in FIG. 7.

Figure 16:
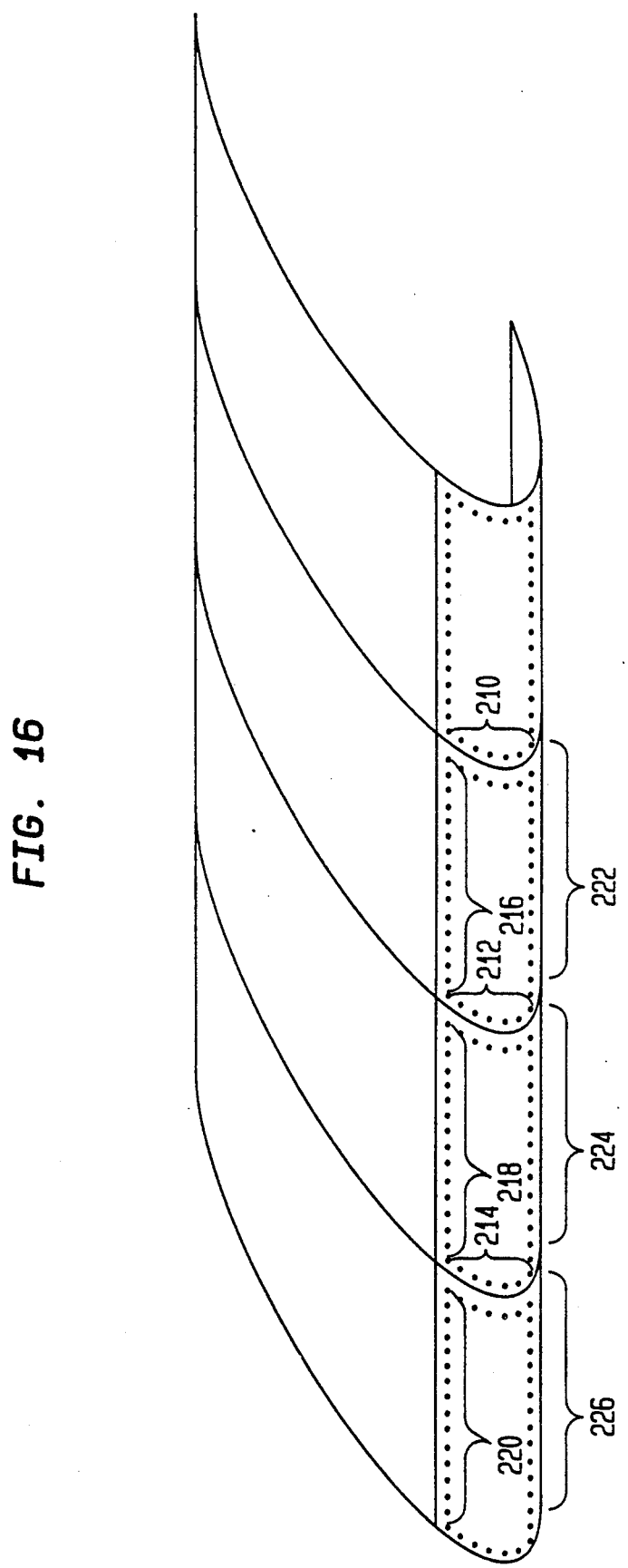
FIG. 16 depicts an aircraft wing cuff structure with rivit lines.
Figure 17:
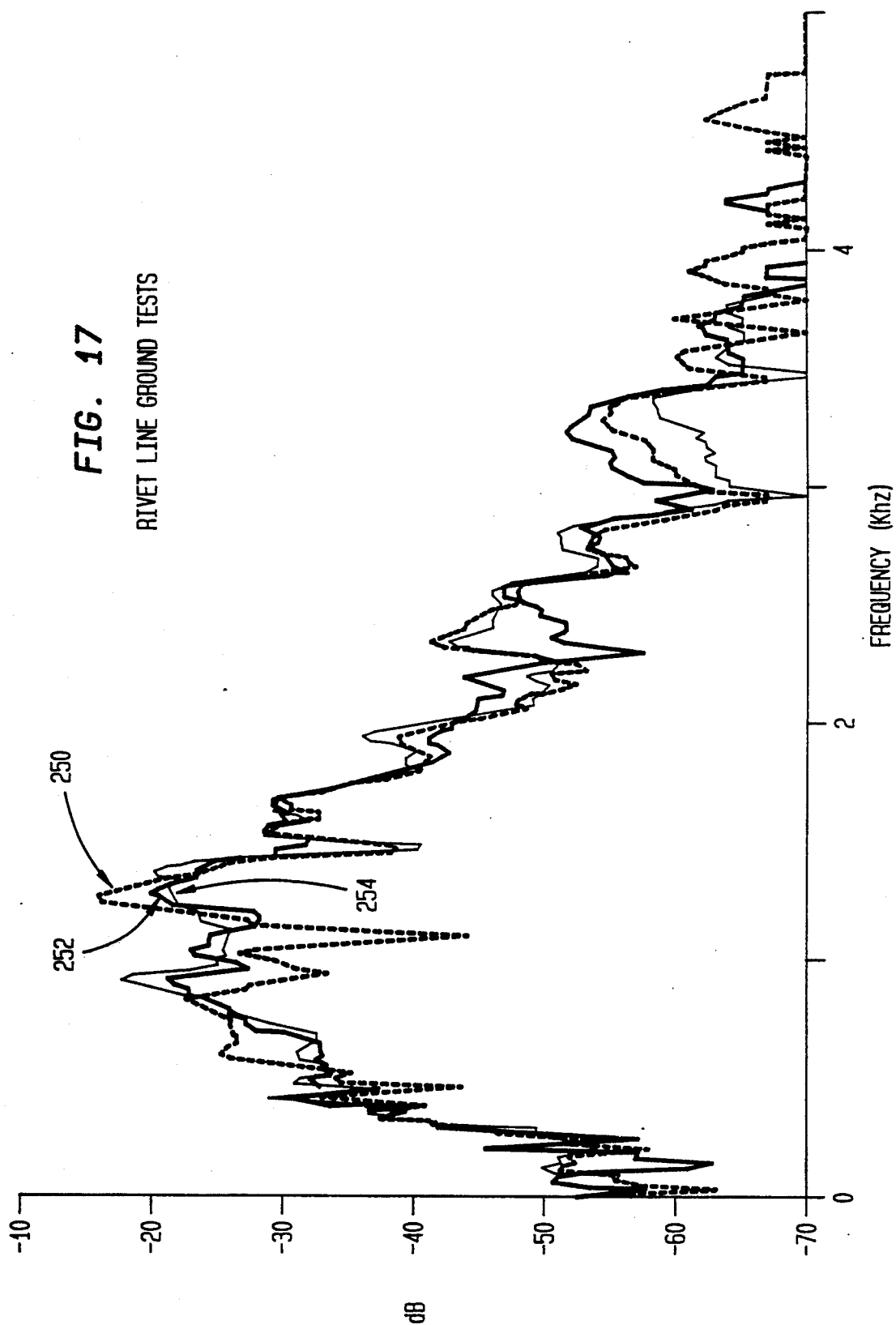
FIG. 17, 18 depict frequency and time data from rivit line failure training.
Figure 18:
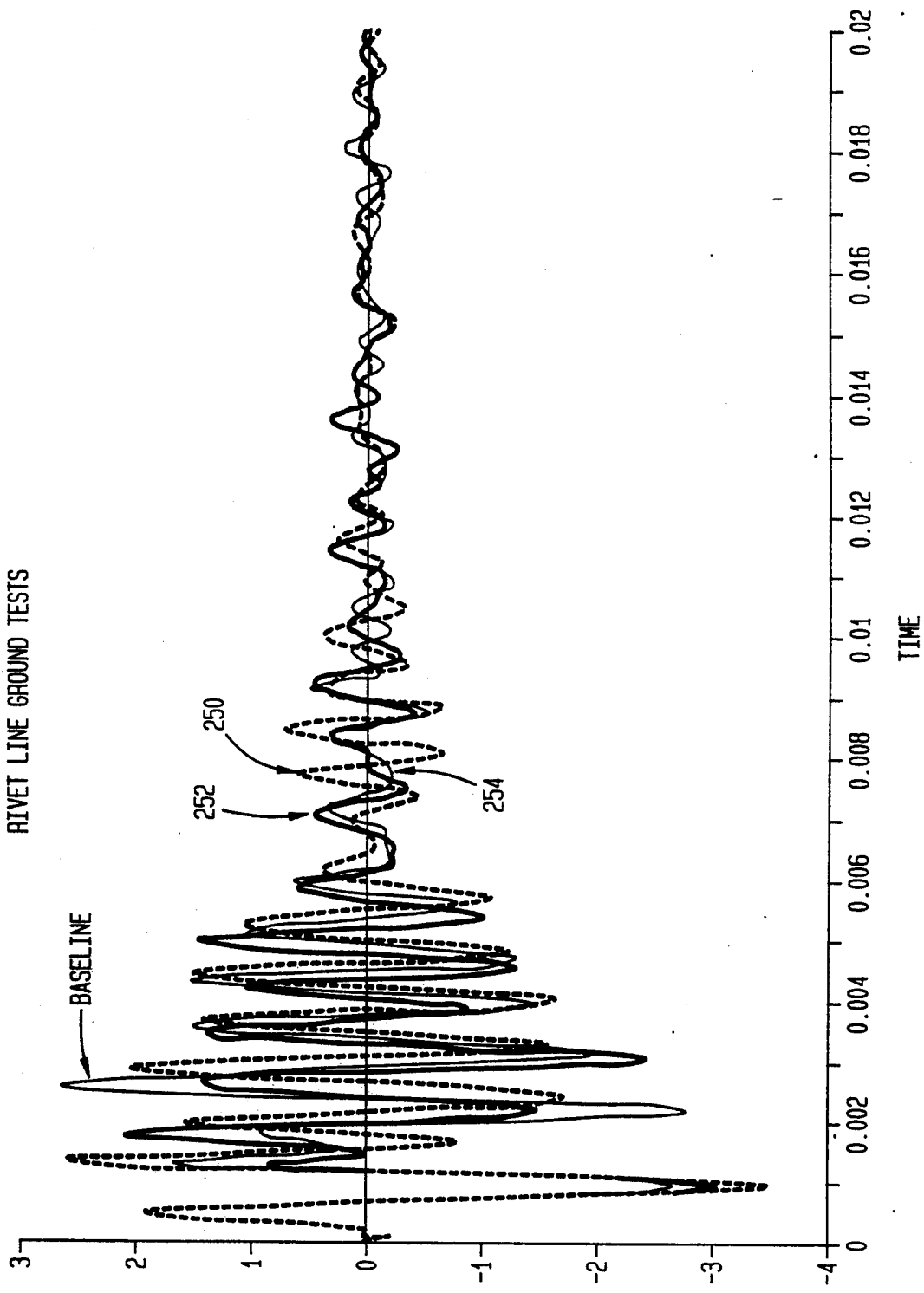
Figure 19:
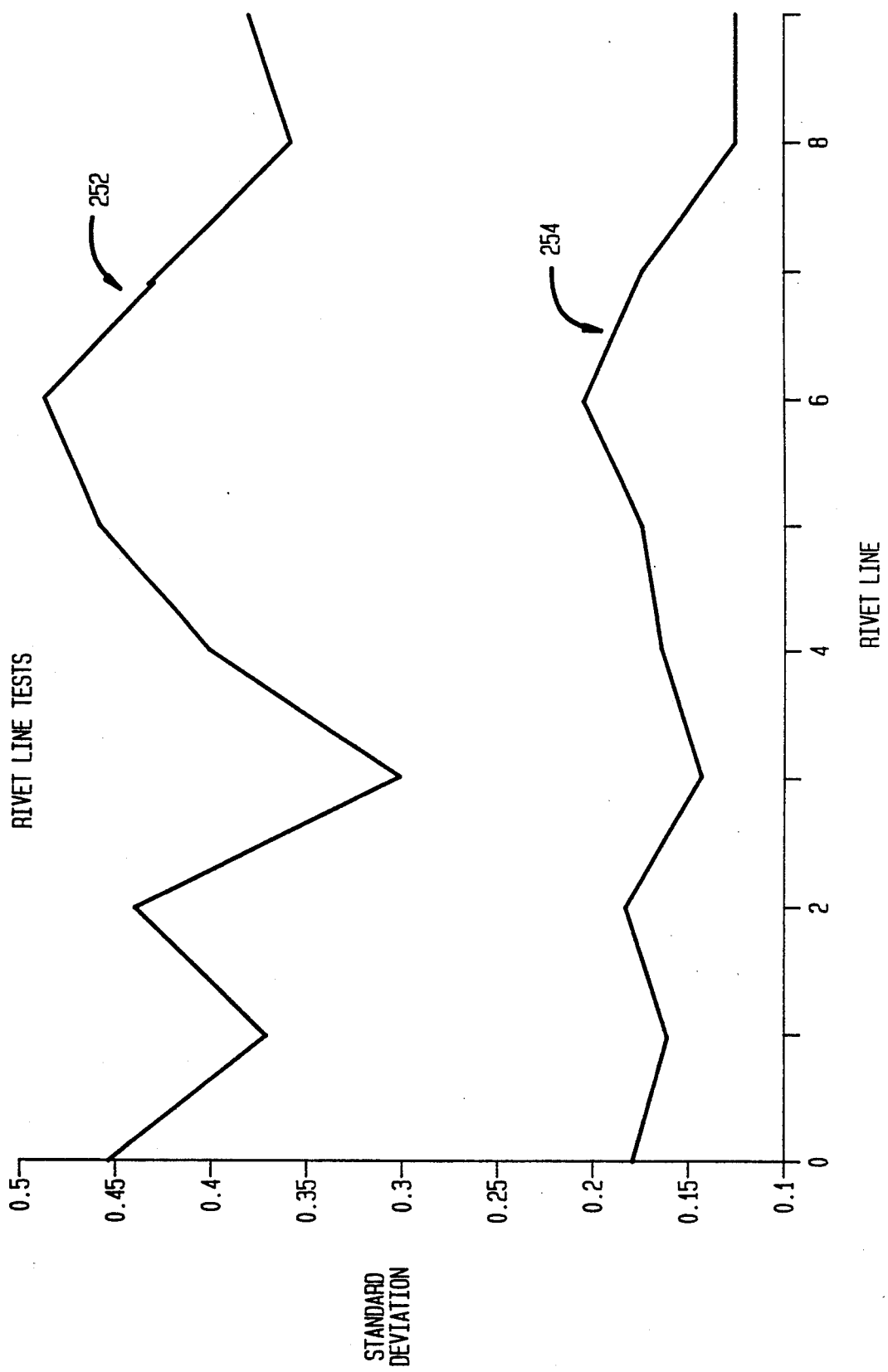
FIGS. 19, 20 depict rivit line features versus failure location.
Figure 20:
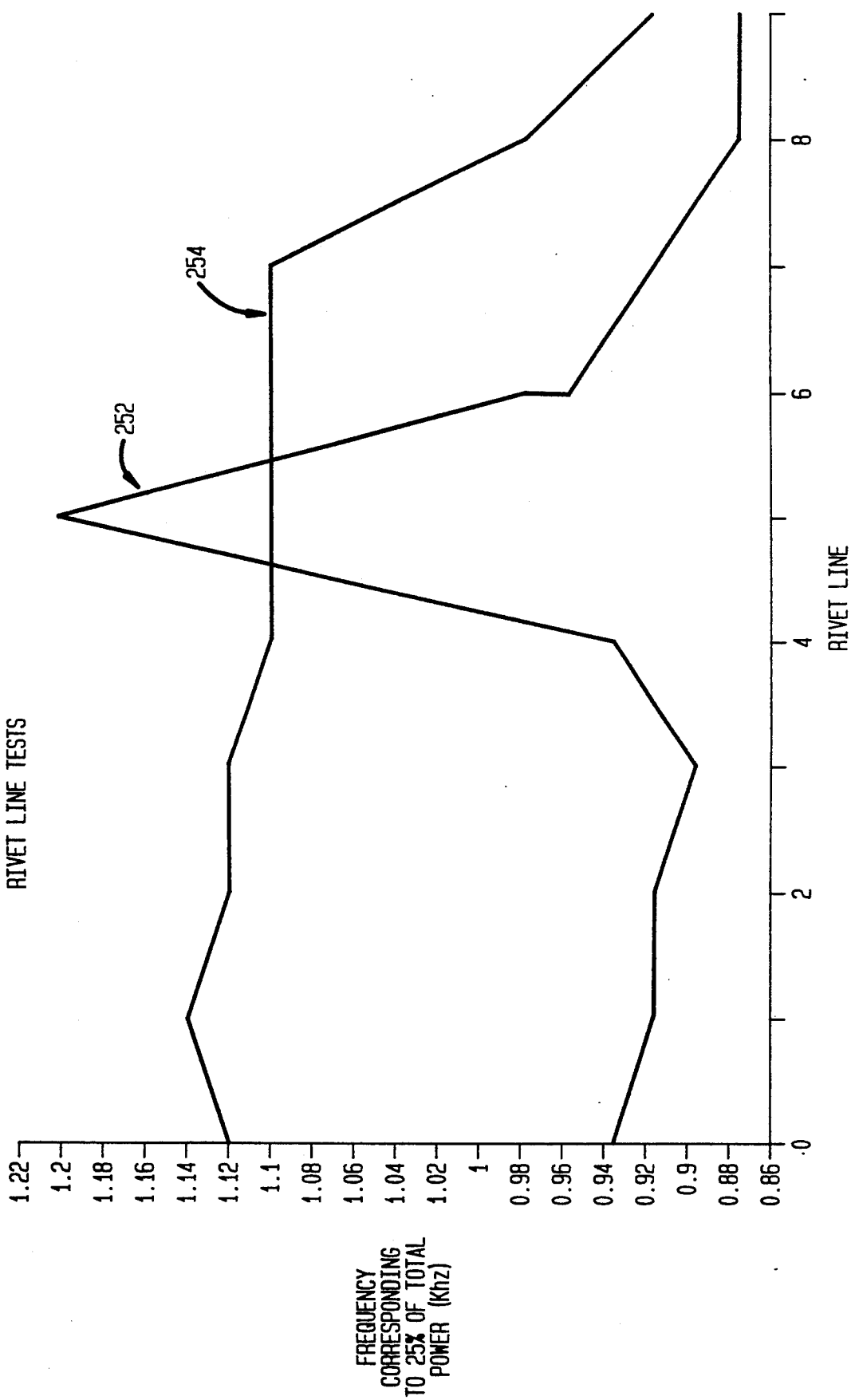

An aircraft wing cuff structure with removable rivit line screws was used to test the centralized health monitoring system described in FIG. 2 and to identify simulated structural faults. FIG. 16 depicts the leading edge wing cuff that was tested for rivit line failure using the HMS and selected pattern recognition features. Rivit lines 210, 212, 214, 216, 218, 220, 222, 224 and 226 were selectively removed and replaced to train the pattern recognition software. FIG. 17 depicts frequency signature data obtained from training the system with rivit lines 216 and 218 failed, while FIG. 18 depicts time signature data obtained from training the system with rivit lines 216 and 218 failed. In each of these figures, line 250 represents a baseline while line 252 represents data from a first sensor and line 254 represents data from a second sensor. Figs. 19 and 20 show selected features plotted as a function of rivit line failure location for two sensors corresponding to lines 252, 254. Rivit lines 1, 2, 3, 4, 5, 6, 7, 8, 9 of FIGS. 19, 20 correspond to rivit lines 210, 212, 214, 216, 218, 220, 222, 224, 226, respectively, of FIG. 16. Both ground and flight test results have shown that the sensors reliably locate which rivet line had failed on the cuff using the pattern recognition software algorithm described in conjunction with FIG. 7.

Figure 21:
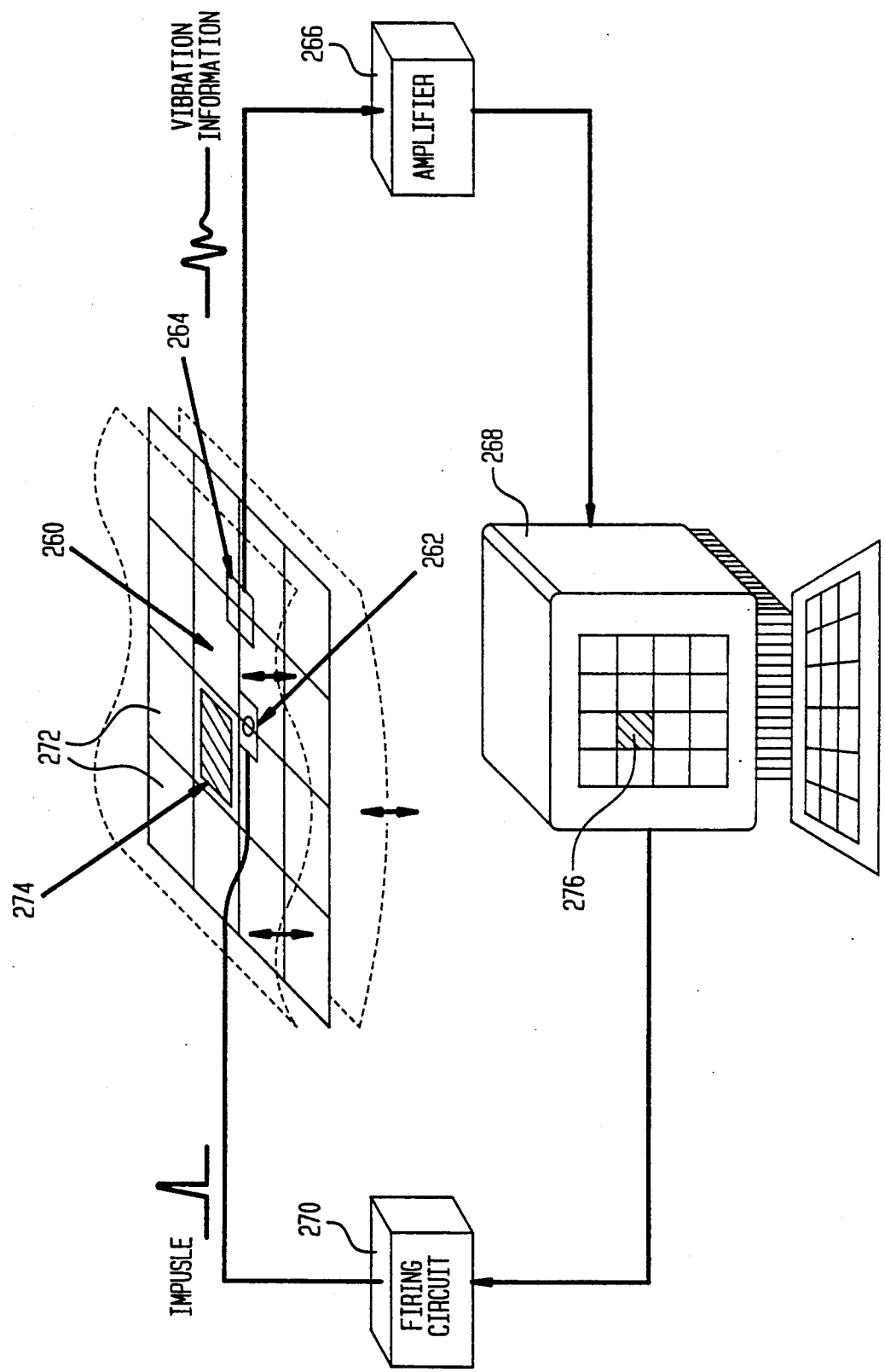
FIG. 21 depicts another embodiment of a monitoring-/control system in accordance with the present invention.

As will be appreciated, the present invention may be employed in a multi-input panel switch to monitor structural parameters or influences associated with the panel, or to control inputs to numerous devices, or to control the switching of numerous devices, or to identify the location and magnitude of a disturbance on a structure, as illustrated in FIG. 21.

More specifically, FIG. 21 depicts a control system comprising panel switch 260, actuation means 262, feedback sensor 264, amplifier 266, computer 268 and firing circuit 270. Computer 268 includes pattern recognition software. Firing circuit 270 includes a high voltage power source as well as switching gate means such as an SCR. Actuation means 262 illustratively includes coil means. Panel switch 260 may be viewed as having a plurality of grid squares 272. Panel switch 260 is typically a flat plate or thin structure, although it need not be.

By attachment of a single actuator 262 and a single dynamic strain sensor 264, such as the piezoelectric sensor of FIGS. 3–4, to the panel surface, signals can be acquired and processed to determine the presence and magnitude of mass or pressure on the panel's surface, as well as the location of the mass or pressure. Computer 268 is used to control the panel switch by first exciting a portion of the panel with an electrical impulse force generated by firing circuit 270 and provided to actuator 262 to produce a mechanical impulse force. The resultant structural vibration is detected by sensor 264 which generates a corresponding electrical signal that is conditioned by amplifier 266 and digitized by an ADC of computer 268. This signal is then processed by pattern recognition software of the type described in FIG. 7 to determine the location and/or magnitude of the force applied to the panel's surface. As depicted in FIG. 21, a grid square 276 is graphically depicted on the computer screen and corresponds to grid square 274 of panel switch 260 which has an external force applied thereto. Of course, the external force need not be applied directly over the actuator or the sensor to be identified by its magnitude and location. As previously described, the system first goes through a training session to teach the computer the phenomena it is supposed to detect or discriminate, as well as to identify a baseline or resting state of the system. This system enables one to perform switching over wide areas with a multitude of inputs without conventional complex mechanical components. Advantageously, the location as well as the magnitude of a force can be determined by using a single sensor and actuator. Illustratively, such a force can be due to finger pressure on a single grid square, a hand "signature" in which a hand is pressed against a plurality of grid squares, an object resting on one or more grid squares, etc.

We claim:

1. An apparatus for monitoring and identifying disturbances to a structure comprising:
   a) first processing means for processing signals so as to monitor and identify disturbances to said structure;
   b) switch means controlled by said first processing means for gating a voltage signal;
   c) actuation means for applying a physical impulse to said structure upon receiving said voltage signal gated by said switch means, wherein the application of said physical impulse to said structure by said actuation means results in said structure experiencing an initial force of magnitude "F" in a first direction followed by a plurality of reactive forces in a direction opposite said first direction and having a total magnitude of "F" wherein said plurality of forces are applied to said structure at positions away from where said force of magnitude "F" was applied;
   d)سensor means for detecting the effects of said physical impulse on said structure and outputting an analog signal, said effects of said physical impulse indicative of said disturbances on said structure;
   e) second processing means for converting said analog signal into a digital signal; and
   f) means for providing said digital signal to said first processing means so as to monitor and identify disturbances to said structure.

2. The apparatus of claim 1 further comprising a high voltage power supply coupled to said switch means wherein said first processing means causes said switch means to gate said voltage signal from said high voltage power supply to said actuation means.

3. The apparatus of claim 1 further comprising pattern recognition means for determining the nature of said disturbance applied to said structure.

4. The apparatus of claim 3 further comprising display means for graphically indicating said disturbance applied to the structure.

5. The apparatus of claim 1 wherein said forces produce a surface wave of wavelength "L" on said structure, "L" being twice the distance separating where said initial force was applied and where an average force of said plurality of reactive forces was applied.

6. The apparatus of claim 5 wherein each of said actuation means has associated therewith two sensor means placed on opposite sides of said actuation means at a distance of "L" from a center of said actuation means.

7. The apparatus of claim 6 wherein said actuation means is circular in shape.

8. The apparatus of claim 1 wherein said first processing means is a microprocessor and said second processing means is an amplifier/conditioner circuit which amplifies and digitizes said analog signal to produce a digital signal.

9. The apparatus of claim 8 further comprising:
   g) a host central processing unit for performing signature pattern analysis; and
   h) a plurality of said apparatuses, each being connected to said host central processing unit and being controlled by said host central processing unit.

10. The apparatus of claim 9 wherein said host central processing unit is connected to each of said apparatuses by a digital signal bus.

11. The apparatus of claim 10 wherein said digital signal bus comprises:
   1) a power line;
   2) a power ground line;
   3) a serial-in communication line;
   4) a serial-out communication line;
   5) a serial ground line;
   6) a reset line; and
   7) an address line.

12. The apparatus of claim 8 further comprising:
   g) an energy storage means for supplying said voltage signal gated by said switch means to said actuation means; and
   h) means for charging said energy storage means to a voltage level greater than a voltage level of a power supply which powers said charging means.

13. The apparatus of claim 12 wherein said charging means is a DC-DC converter.

14. The apparatus of claim 12 wherein said actuation means comprises a pair of electromagnetic coils separated by a gap and configured such that application of said voltage signal causes said gap to change in size thereby applying said physical impulse to said structure.

15. The apparatus of claim 14 wherein each of said coils comprises a flat spiral metalization layer.

16. The apparatus of claim 12 wherein said sensor means comprises a piezoelectric sensor.

17. The apparatus of claim 16 wherein said piezoelectric sensor comprises a polarized polyvinylidene fluoride layer, a first low resistance contact on one side of said layer, and a second low resistance contact on another side of said layer.

18. The apparatus of claim 16 further comprising a housing in which said apparatus is embedded.

19. A method of monitoring and identifying icing on and fatigue to a structure comprising the steps of:
  a) acquiring and storing at least one of time and frequency domain signatures of known failure modes of said structure; and
  b) forming a database of patterns which are correlated to icing conditions, wherein said step of forming employs pattern recognition software, said software being employed to perform the steps of:
    i) generating features;
    ii) analyzing histograms; and
    iii) classifying signals,
so as to enable a processor to make icing and fatigue measurements on said structure by correlating at least one of said time and frequency domain signatures of said known failure modes with at least one of time and frequency domain signals obtained from said structure.

20. An apparatus for monitoring and identifying disturbances to a structure comprising:
  a) first processing means for processing signals so as to monitor and identify disturbances to said structure;
  b) a plurality of switch means each separately controlled by said first processing means for gating a voltage signal;
  c) a plurality of actuation means each coupled to one of said plurality of switch means for applying a physical impulse to said structure upon receiving a voltage signal gated by the switch means to which it is coupled, each of said plurality of actuation means having a pair of electromagnetic coils separated by a gap and configured such that an application of said voltage signal causes said gap to change, thereby applying said physical impulse to said structure;
  d) a plurality of sensor means attached to various portions of said structure, search for detecting the effects of said physical impulse on said structure and outputting an analog signal, said effects of said physical impulse indicative of disturbances of said structure;
  e) second processing means for converting any one of said analog signals into a corresponding digital signal;
  f) multiplexer means for selectively applying any of said analog signals to said second processing means; and
  g) means for providing any one of said digital signals to said first processing means so as to monitor and identify disturbances to said structure.

21. The apparatus of claim 20 wherein each of said coils comprises a flat spiral metallization layer.

22. The apparatus of claim 20 wherein each of said sensor means comprises a piezoelectric sensor and wherein each of said pairs of coils has associated therewith a plurality of said piezoelectric sensors.

23. The apparatus of claim 20 wherein each of said sensor means comprises a piezoelectric sensor.

24. The apparatus of claim 23 wherein said piezoelectric sensor comprises a polarized polyvinylidene fluoride layer, a first low resistance contact on one side of said layer, and a second low resistance contact on another side of said layer.

25. A method of monitoring and identifying faults and physical disturbance to a structure comprising the steps of:
  a) mechanically exciting said structure so as to induce vibration of said structure;
  b) transducing said vibration so as to produce a first analog signal corresponding to said vibration;
  c) deriving a baseline vibration signal from said first analog signal, said baseline vibration signal representing a baseline or normal response of said structure;
  d) monitoring said structure by transducing said physical disturbances so as to produce a second analog signal corresponding to said faults and physical disturbances;
  e) deriving another vibration signal from second analog signal, said another vibration signal representing a response of said structure due to said faults and physical disturbances;
  f) obtaining a first plurality of features from said baseline vibration signal, said feature being influenced by the nature of said structure;
  g) obtaining a second plurality of features from said another vibration signal, said features being influenced by the nature of said structure; and
  h) analyzing said first plurality and said second plurality of features so as to monitor and identify the nature and extent of said faults and physical disturbances, wherein said step of analyzing is performed in a pattern space of a plurality of known features which are known to be indicative of specific disturbances and faults.

26. The method of claim 25 wherein said analyzing comprises analyzing in a frequency domain and in a time domain.

27. The method of claim 25 wherein said disturbances and faults comprise at least some of the group of ice accretion, fatigue, stress, corrosion, structural damage and cracks.

28. The apparatus of claim 25 wherein said known features are selected from the group of amplitude ratios of power spectrum signals, frequencies of signals, frequency differences of signals, partial energies, ratio of partial energies, number of power spectrum peaks exceeding a threshold, frequencies at which various percentages of total energy are observed, damping numbers, a percentage of a demodulation period, standard deviation, kurtosis, skewness, decay time, mode shapes and total energy.

29. An apparatus for monitoring and detecting faults in a structure comprising:
  a) a continuity sensor comprising a first low resistance layer, said first low resistance layer being in the form of at least one elongated low resistance path having a first electrode and having first and second ends; and
  b) a dynamic strain sensor adapted for attachment to a surface of said structure and having:
    i) a first piezoelectric layer; and
    ii) said first low resistance layer, said first electrode being attached to one side of said piezoelectric layer and electrically insulated from said structure, wherein an opposite side of said piezoelectric layer is adapted for attachment to said structure which forms a second low resistance layer, and continuity faults are detected by monitoring electrical resistance between said first and second ends, and strains are detected by monitoring said first low resistance layer and said second low resistance layer for electrical signals, wherein a capacitance value of said dynamic strain sensor is determined by a dielectric constant of said piezoelectric layer, a distance separating said first electrode from said second low resistance contact, and a surface area of said first electrode attached to said piezoelectric layer, and wherein the measured electrical resistance, strain, and capacitance vary in accordance with the nature and extent of the faults in the structure to be monitored and detected.

30. The apparatus of claim 29 further comprising a plurality of such apparatuses connected in series wherein a location of a continuity fault in said first low resistance layer may be determined by measuring a capacitance value of the series connection of said apparatuses.

31. An apparatus for monitoring and detecting faults in a structure comprising:
   a) a continuity sensor comprising a first low resistance layer, said first low resistance layer being in the form of at least one elongated low resistance path having a first electrode and having first and second ends; and
   b) a dynamic strain sensor adapted for attachment to a surface of said structure and having:
      i) a piezoelectric layer attached to said first low resistance layer; and
      ii) a second low resistance layer attached to an opposite side of said piezoelectric layer and adapted for attachment to said structure,
   wherein continuity faults are detected by monitoring electrical resistance between said first and second ends, strains and detected by monitoring said first low resistance layer and said second resistance layer for electrical signals, and a capacitance value of said dynamic strain sensor is determined by a dielectric constant of said piezoelectric layer, a distance separating said first electrode from said second low resistance contact, and surface area of said first electrode attached to said piezoelectric layer, and wherein the measured electrical resistance, strain, and capacitance vary in accordance with the nature and extent of the faults in the structure to be monitored and detected.

32. The apparatus of claim 31 further comprising a plurality of such apparatuses connected in series wherein a location of a continuity fault in said first low resistance layer may be determined by measuring a capacitance value of the series connection of said apparatuses.

33. An apparatus for monitoring strains in a structure comprising:
   a) a piezoelectric layer which produces electrical signals in response to application of a dynamic force to said layer; and
   b) a first low resistance layer attached on one side to a first side of said piezoelectric layer, and adapted for attachment to said structure on another side;
   c) a second low resistance layer attached to a second side of said piezoelectric layer; and
   d) means for monitoring said first and second low resistance layers for electrical signals so as to determine the existence and extent of strains experienced by said structure.

34. The apparatus of claim 33 wherein said monitoring means comprises a digital signal processor and pattern recognition means for identifying the cause of said strains.

35. An apparatus for monitoring strains in a structure comprising:
   a) a piezoelectric layer which produces electrical signals in response to application of a dynamic force to said layer; and
   b) a first low resistance layer attached on one side to a first side of said piezoelectric layer, and adapted for attachment to said structure on another side;
   c) a second low resistance layer attached to a second side of said piezoelectric layer; and
   d) means for detecting a capacitance value of said piezoelectric layer by determining the capacitance between said first and second low resistance layers so as to determine the existence and extent of strains experienced by said structure.

36. An apparatus for monitoring and identifying disturbances to a structure comprising:
   a) first processing means for processing signals so as to monitor and identify disturbances to said structure;
   b) switch means controlled by said first processing means for gating a voltage signal;
   c) actuation means for applying a physical excitation to said structure upon receiving said voltage signal gated by said switch means, wherein the application of said physical excitation to said structure by said actuation means results in said structure experiencing an initial force of magnitude "F" in a first direction followed by a plurality of reactive forces in a direction opposite said first direction and having a total magnitude of "F" wherein said plurality of forces are applied to said structure at positions away from where said force of magnitude "F" was applied;
   d) sensor means for detecting the effects of said physical excitation on said structure and outputting an analog signal, said effects of said physical excitation indicative of said disturbances on said structure;
   e) second processing means for converting said analog signal into a digital signal; and
   f) means for providing said digital signal to said first processing means so as to monitor and identify disturbances to said structure.

* * * * *